(12) United States Patent
Grødeland et al.

(10) Patent No.: US 12,005,112 B2
(45) Date of Patent: Jun. 11, 2024

(54) VACCINE MOLECULES

(71) Applicant: University of Oslo, Oslo (NO)

(72) Inventors: Gunnveig Grødeland, Oslo (NO); Bjarne Bogen, Oslo (NO); Ane Marie Anderson, Oslo (NO)

(73) Assignee: University of Oslo, Oslo (NO)

( * ) Notice: Subject to any disclaimer, the term of this patent is extended or adjusted under 35 U.S.C. 154(b) by 1105 days.

(21) Appl. No.: 16/645,135

(22) PCT Filed: Sep. 7, 2018

(86) PCT No.: PCT/IB2018/001202
§ 371 (c)(1),
(2) Date: Mar. 6, 2020

(87) PCT Pub. No.: WO2019/048936
PCT Pub. Date: Mar. 14, 2019

(65) Prior Publication Data
US 2021/0069319 A1    Mar. 11, 2021

Related U.S. Application Data

(60) Provisional application No. 62/555,300, filed on Sep. 7, 2017.

(51) Int. Cl.
| | | |
|---|---|---|
| *A61K 39/145* | (2006.01) | |
| *A61P 31/16* | (2006.01) | |
| *C07K 14/005* | (2006.01) | |
| *C07K 16/28* | (2006.01) | |
| *A61K 39/00* | (2006.01) | |

(52) U.S. Cl.
CPC ............ *A61K 39/145* (2013.01); *A61P 31/16* (2018.01); *C07K 14/005* (2013.01); *C07K 16/2833* (2013.01); *A61K 2039/53* (2013.01); *A61K 2039/575* (2013.01); *C07K 2317/526* (2013.01); *C07K 2317/53* (2013.01); *C07K 2317/622* (2013.01); *C07K 2319/33* (2013.01); *C07K 2319/40* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 4,596,556 | A | 6/1986 | Morrow et al. |
| 4,675,189 | A | 6/1987 | Kent et al. |
| 5,057,540 | A | 10/1991 | Kensil et al. |
| 5,075,109 | A | 12/1991 | Tice et al. |
| 5,133,974 | A | 7/1992 | Paradissis et al. |
| 5,284,656 | A | 2/1994 | Platz et al. |
| 5,407,686 | A | 4/1995 | Patel et al. |
| 5,451,569 | A | 9/1995 | Wong et al. |
| 5,736,152 | A | 4/1998 | Dunn |
| 5,993,412 | A | 11/1999 | Deily et al. |
| 6,005,099 | A | 12/1999 | Davies et al. |
| 6,651,655 | B1 | 11/2003 | Licalsi et al. |
| 7,482,430 | B2 | 1/2009 | Wiley |
| 8,932,603 | B2 | 1/2015 | Bogen et al. |
| 2005/0238660 | A1 | 10/2005 | Babiuk et al. |
| 2005/0281843 | A1 | 12/2005 | Singh et al. |
| 2010/0168390 | A1 | 7/2010 | Brix et al. |
| 2013/0171140 | A1 | 7/2013 | Ruffini et al. |
| 2014/0234316 | A1 | 8/2014 | Bogen et al. |

FOREIGN PATENT DOCUMENTS

| | | |
|---|---|---|
| EP | 0468520 | 1/1992 |
| EP | 0517565 | 5/1992 |
| EP | 1599504 | 11/1992 |
| EP | 0362279 | 1/1995 |
| EP | 0549074 | 1/1999 |
| EP | 0729473 | 8/2000 |
| EP | 0689454 | 2/2005 |
| WO | WO 92/19265 | 11/1992 |
| WO | WO 93/13202 | 7/1993 |
| WO | WO 94/00153 | 1/1994 |
| WO | WO 95/17210 | 6/1995 |
| WO | WO 96/02555 | 2/1996 |
| WO | WO 96/11711 | 4/1996 |
| WO | WO 96/33739 | 10/1996 |
| WO | WO 97/48440 | 12/1997 |

(Continued)

OTHER PUBLICATIONS

Grodeland et al. (Journal of Immunology, 2013, vol. 191, p. 3221-3231).*
Grodeland et al. (Journal of Immunology, 2013, vol. 191, p. 3221-3231 of record on Feb. 13, 2023).*
Gunnveig Grodeland et al. "Antigen Targeting to Human HLA Class II Molecules Increases Efficacy of DNA Vaccination" The Journal of Immunology, vol. 197, No. 9, Sep. 26, 2016, pp. 3575-3585.
Huber V C et al. "A multi-valent vaccine approach that elicits broad immunity within an influenza subtype" Vaccine, Elsevier, NL, vol. 27, No. 8, Feb. 18, 2009, pp. 1192-1200.
S.S. Rao et al. "A gene-based avian influenza vaccine in poultry" Poultry Science, vol. 88, No. 4, Apr. 1, 2009, pp. 860-866.
Mookkan Prabakaran et al. "Progress toward a Universal H5N1 Vaccine: A Recombinant Modified Vaccinia Virus Ankara-Expressing Trivalent Hemagglutinin Vaccine" Plos One, vol. 9, No. 9, Sep. 17, 2014, p. e107316.

(Continued)

*Primary Examiner* — Agnieszka Boesen
(74) *Attorney, Agent, or Firm* — Casimir Jones, S.C.; J. Mitchell Jones

(57) ABSTRACT

Provided herein is technology relating to vaccines and particularly, but not exclusively, to compositions, methods, and uses of a mixture of immunogenic vaccine molecules comprising components for targeting the dimeric vaccine molecules to antigen-presenting cells and components for eliciting an immunogenic response, wherein the components for eliciting an immunogenic response preferably comprise at least three variants of an immunogenic protein, such as variants of immunogenic proteins obtained from three or more different strains of a pathogenic organism.

19 Claims, 10 Drawing Sheets

Figure 3:
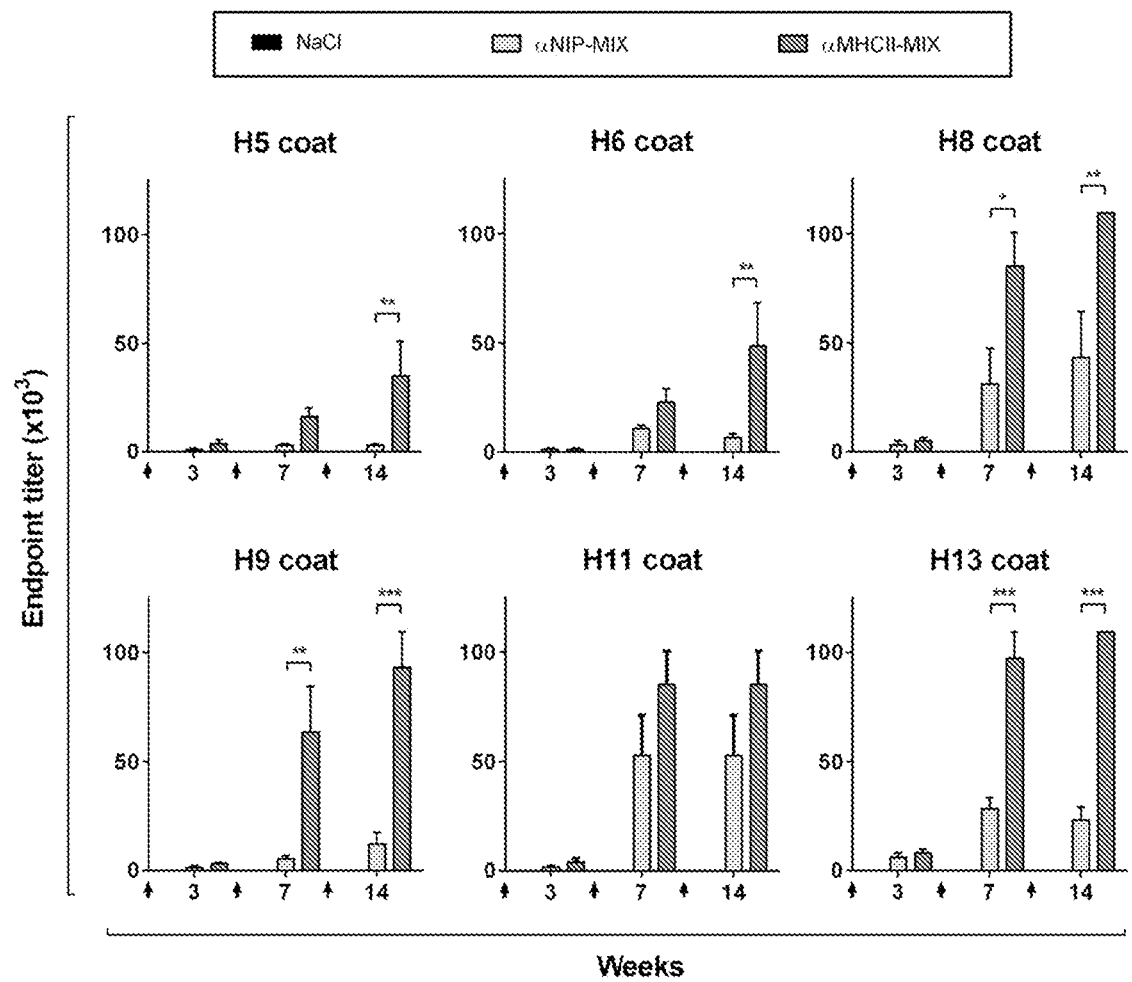

Specification includes a Sequence Listing.

(56) References Cited

FOREIGN PATENT DOCUMENTS

| WO | WO 98/16247 | 4/1998 |
|---|---|---|
| WO | WO 98/20734 | 5/1998 |
| WO | WO 98/28037 | 7/1998 |
| WO | WO 98/56414 | 12/1998 |
| WO | WO 99/10008 | 3/1999 |
| WO | WO 99/11241 | 3/1999 |
| WO | WO 99/12565 | 3/1999 |
| WO | WO 99/27961 | 6/1999 |
| WO | WO 2001/049866 | 7/2001 |
| WO | 03/057921 | 7/2003 |
| WO | WO 03/095022 | 11/2003 |
| WO | WO 2004/076489 | 9/2004 |
| WO | 2008/048984 | 4/2008 |
| WO | 2011/161244 | 12/2011 |
| WO | 2013/041966 | 3/2013 |
| WO | 2013/092875 | 6/2013 |

OTHER PUBLICATIONS

Ane Marie Anderson et al. "Simultaneous Targeting Multiple Hemagglutinins to APCs for Induction of Broad Immunity against Influenza" The Journal of Immunology, vol. 200, No. 6, Feb. 2, 2018, pp. 2057-2066.
International Search Report & Written Opinion, Appl. No. PCT/IB2018/001202, dated Jan. 15, 2019, 17 pages.

Adjei et al., Bioavailability of leuprolide following intratracheal administraion to beagle dogs. Int. J. Pharmaceutics 1990; 63:135-144.

Adjei et al., Pulmonary delivery of peptide drugs: effect of particle size on bioavailability of leuprolide acetate in healthy male volunteers. Pharm Res. Jun. 1990;7(6):565-9.

AIR. Sequence relationships among the hemagglutinin genes of 12 subtypes of influenza A virus. Proc Natl Acad Sci U S A. Dec. 1981;78(12):7639-43.

Batista et al., B cells acquire antigen from target cells after synapse formation. Nature. May 24, 2001;411(6836): 489-94.

Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. Dec. 16, 2002;196(12):1627-38.

Braquet, et al. Effect of endothelin-1 on blood pressure and bronchopulmonary system of the guinea pig. J Cardiovasc Pharmacol. 1989;13 Suppl 5:S143.

Brazolot-Millan et al., CpG DNA can induce strong Th1 humoral and cell-mediated immune responses against hepatitis B surface antigen in young mice. Proc Natl Acad Sci U S A. Dec. 22, 1998;95(26):15553-8.

Broderick et al., Electroporation-enhanced delivery of nucleic acid vaccines. Expert Rev Vaccines. Feb. 2015;14(2):195-204.

Caminschi et al., The dendritic cell subtype-restricted C-type lectin Clec9A is a target for vaccine enhancement. Blood. Oct. 15, 2008;112(8):3264-73.

Carayanniotis et al., Adjuvant-free IgG responses induced with antigen coupled to antibodies against class II MHC. Nature. May 7-13, 1987;327(6117):59-61.

Chen et al., The first avian influenza A (H7N9) viral infection in humans in Zhejiang Province, China: a death report. Front Med. Sep. 2013;7(3):333-44.

Davis et al., CpG DNA is a potent enhancer of specific immunity in mice immunized with recombinant hepatitis B surface antigen. J Immunol. Jan. 15, 1998;160(2):870-6.

Debs et al., Lung-Specific delivery of cytokines induces sustained pulmonary and systemic immunomodulation in rats. J. Immunol. 1988;140:3482-3488.

Diazgranados et al., Seasonal influenza vaccine efficacy and its determinants in children and non-elderly adults: a systematic review with meta-analyses of controlled trials. Vaccine. Dec. 17, 2012;31(1):49-57.

Dilillo et al., Broadly neutralizing hemagglutinin stalk-specific antibodies require FcγR interactions for protection against influenza virus in vivo. Nat Med. Feb. 2014;20(2):143-51.

Fineberg. Pandemic preparedness and response—lessons from the H1N1 influenza of 2009. N Engl J Med. Apr. 3, 2014;370(14):1335-42.

Fossum et al., Vaccine molecules targeting Xcr1 on cross-presenting DCs induce protective CD8+ T-cell responses against influenza virus. Eur J Immunol. Feb. 2015;45(2):624-35.

Fredriksen et al., Chemokine-idiotype fusion DNA vaccines are potentiated by bivalency and xenogeneic sequences. Blood. Sep. 15, 2007;110(6):1797-805.

Fredriksen et al., DNA vaccines increase immunogenicity of idiotypic tumor antigen by targeting novel fusion proteins to antigen-presenting cells. Mol Ther. Apr. 2006;13(4):776-85.

Fredriksen et al., Targeted DNA vaccines for enhanced induction of idiotype-specific B and T cells. Front Oncol. Oct. 30, 2012;2:154.

Greenberg et al., Lymphocyte cytotoxicity to influenza virus-infected cells: response to vaccination and virus infection. Infect Immun. Jun. 1978;20(3):640-5.

Grodeland et al., Antigen Targeting to Human HLA Class II Molecules Increases Efficacy of DNA Vaccination. J Immunol. Nov. 1, 2016;197(9):3575-3585.

Grodeland et al., DNA vaccine that targets hemagglutinin to MHC class II molecules rapidly induces antibody-mediated protection against influenza. J Immunol. Sep. 15, 2013;191(6):3221-31.

Grodeland et al., Efficient vaccine against pandemic influenza: combining DNA vaccination and targeted delivery to MHC class II molecules. Expert Rev Vaccines. Jun. 2015;14(6):805-14.

Grodeland et al., Polarizing T and B Cell Responses by APC-Targeted Subunit Vaccines. Front Immunol. Jul. 20, 2015;6:367. 7 pages.

Grodeland et al., The specificity of targeted vaccines for APC surface molecules influences the immune response phenotype. PLoS One. Nov. 11, 2013;8(11):e80008. 11 pages.

Hashimoto et al., Antibody-dependent cell-mediated cytotoxicity against influenza virus-infected cells. J Infect Dis. Nov. 1983;148(5):785-94.

Hien et al., Avian influenza A (H5N1) in 10 patients in Vietnam. N Engl J Med. Mar. 18, 2004;350(12):1179-88.

Hilgers et al., Synergistic effects of synthetic adjuvants on the humoral immune response. Int Arch Allergy Appl Immunol. 1986;79(4):392-6.

Hilgers et al., Synthetic sulpholipopolysaccharides: novel adjuvants for humoral immune responses. Immunology. Jan. 1987;60(1):141-6.

Huang et al., Human infection with an avian influenza A (H9N2) virus in the middle region of China. J Med Virol. Oct. 2015;87(10):1641-8.

Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.

Illum et al., Hyaluronic acid ester microspheres as a nasal delivery system for insulin. J. Controlled Rel., 1994, 29:133-141.

Jegaskanda et al., Cross-reactive influenza-specific antibody-dependent cellular cytotoxicity antibodies in the absence of neutralizing antibodies. J Immunol. Feb. 15, 2013;190(4):1837-48.

Kabanova et al., Antibody-driven design of a human cytomegalovirus gHgLpUL128L subunit vaccine that selectively elicits potent neutralizing antibodies. Proc Natl Acad Sci U S A. Dec. 16, 2014;111(50):17965-70.

Kensil et al., Separation and characterization of saponins with adjuvant activity from Quillaja saponaria Molina cortex. J Immunol. Jan. 15, 1991;146(2):431-7.

Kensil, Saponins as vaccine adjuvants. Crit Rev Ther Drug Carrier Syst. 1996;13(1-2):1-55.

Lacaille-Dubois et al., A review of the biological and pharmacological activities of saponins. Phytomedicine. Mar. 1996;2(4):363-86.

(56) References Cited

OTHER PUBLICATIONS

Lu et al., Identification of a CD4 T-cell epitope in the hemagglutinin stalk domain of pandemic H1N1 influenza virus and its antigen-driven TCR usage signature in BALB/c mice. Cell Mol Immunol. Jun. 2017;14(6):511-520.

Mayer et al., TriFabs—Trivalent IgG-Shaped Bispecific Antibody Derivatives: Design, Generation, Characterization and Application for Targeted Payload Delivery. Int J Mol Sci. Nov. 17, 2015;16(11):27497-507.

McCluskie et al., CpG DNA is a potent enhancer of systemic and mucosal immune responses against hepatitis B surface antigen with intranasal administration to mice. J Immunol. Nov. 1, 1998;161(9):4463-6.

Meier et al., Foldon, the natural trimerization domain of T4 fibritin, dissociates into a monomeric A—state form containing a stable beta- hairpin: atomic details of trimer dissociation and local beta-hairpin stability from residual dipolar couplings. J Mol Biol. Dec. 3, 2004;344(4):1051-69.

Mestecky, The common mucosal immune system and current strategies for induction of immune responses in external secretions. J Clin Immunol. Jul. 1987;7(4):265-76.

Norderhaug et al., Versatile vectors for transient and stable expression of recombinant antibody molecules in mammalian cells. J Immunol Methods. May 12, 1997;204(1):77-87.

Oeswein, et al. "Aerosolization of Proteins", 1990; Proceedings of Symposium on Respiratory Drug Delivery II Keystone, Colorado. 34 pages.

Partridge et al., Global production of seasonal and pandemic (H1N1) influenza vaccines in 2009-2010 and comparison with previous estimates and global action plan targets. Vaccine. Jul. 5, 2010;28(30):4709-12.

Perdue et al., The future of cell culture-based influenza vaccine production. Expert Rev Vaccines. Aug. 2011;10(8):1183-94.

Powell et al., Vaccine Design—the Subunit and Adjuvant Approach, Plenum Press, New York, 1995. TOC only. 42 pages.

Raviprakash et al., Needle-free injection of DNA vaccines: a brief overview and methodology. Methods Mol Med. 2006;127:83-9.

Roos et al., Enhancement of cellular immune response to a prostate cancer DNA vaccine by intradermal electroporation. Mol Ther. Feb. 2006;13(2):320-7.

Roos et al., Skin electroporation: effects on transgene expression, DNA persistence and local tissue environment. PLoS One. Sep. 30, 2009;4(9):e7226. 10 pages.

Ruffini et al., Human chemokine MIP1a increases efficiency of targeted DNA fusion vaccines. Vaccine. Dec. 16, 2010;29(2):191-9.

Smith et al., Pulmonary deposition and clearance of aerosolized alpha-1-proteinase inhibitor administered to dogs and to sheep. J Clin Invest. Oct. 1989;84(4):1145-54.

Soleimanpour et al., APC targeting enhances immunogenicity of a novel multistage Fc-fusion tuberculosis vaccine in mice. Appl Microbiol Biotechnol. Dec. 2015;99(24):10467-80.

Spang et al., Heterodimeric barnase-barstar vaccine molecules: influence of one versus two targeting units specific for antigen presenting cells. PLoS One. 2012;7(9):e45393. 10 pages.

Tamura et al., Definition of amino acid residues on the epitope responsible for recognition by influenza A virus H1-specific, H2-specific, and H1- and H2-cross-reactive murine cytotoxic T-lymphocyte clones. J Virol. Nov. 1998;72(11):9404-6.

Terajima et al., Complement-dependent lysis of influenza a virus-infected cells by broadly cross-reactive human monoclonal antibodies. J Virol. Dec. 2011;85(24):13463-7.

To et al., Emergence in China of human diseas due to avian influenza A(H10N8)—cause for concern? J Infect. Mar. 2014;68(3):205-15.

Treanor et al., Safety and immunogenicity of a recombinant hemagglutinin vaccine for H5 influenza in humans. Vaccine. Feb. 8, 2001;19(13-14):1732-7.

Tricco et al., Comparing infuenza vaccine efficacy against mismatched and matched strains: a systematic review and meta-analysis. BMC Med. Jun. 25, 2013;11:153.

Wei et al., Human infection with avian influenza A H6N1 virus: an epidemiological analysis. Lancet Respir Med. Dec. 2013;1(10):771-8.

Wilkinson et al., Preexisting influenza-specific CD4+ T cells correlate with disease protection against influenza challenge in humans. Nat Med. Jan. 29, 2012;18(2):274-80.

Xie et al., A new format of bispecific antibody: highly efficient heterodimerization, expression and tumor cell lysis. J Immunol Methods. Jan. 2005;296(1-2):95-101.

Yap et al., Transfer of specific cytotoxic T lymphocytes protects mice inoculated with influenza virus. Nature. May 18, 1978;273(5659):238-9.

Zapata et al., Engineering linear F(ab')2 fragments for efficient production in *Escherichia coli* and enhanced antiproliferative activity. Protein Eng. Oct. 1995;8(10):1057-62.

Zweerink et al., Cytotoxic T cells kill influenza virus infected cells but do not distinguish between serologically distinct type A viruses. Nature. May 26, 1977;267(5609):354-6.

\* cited by examiner

FIG. 1

FIG. 2
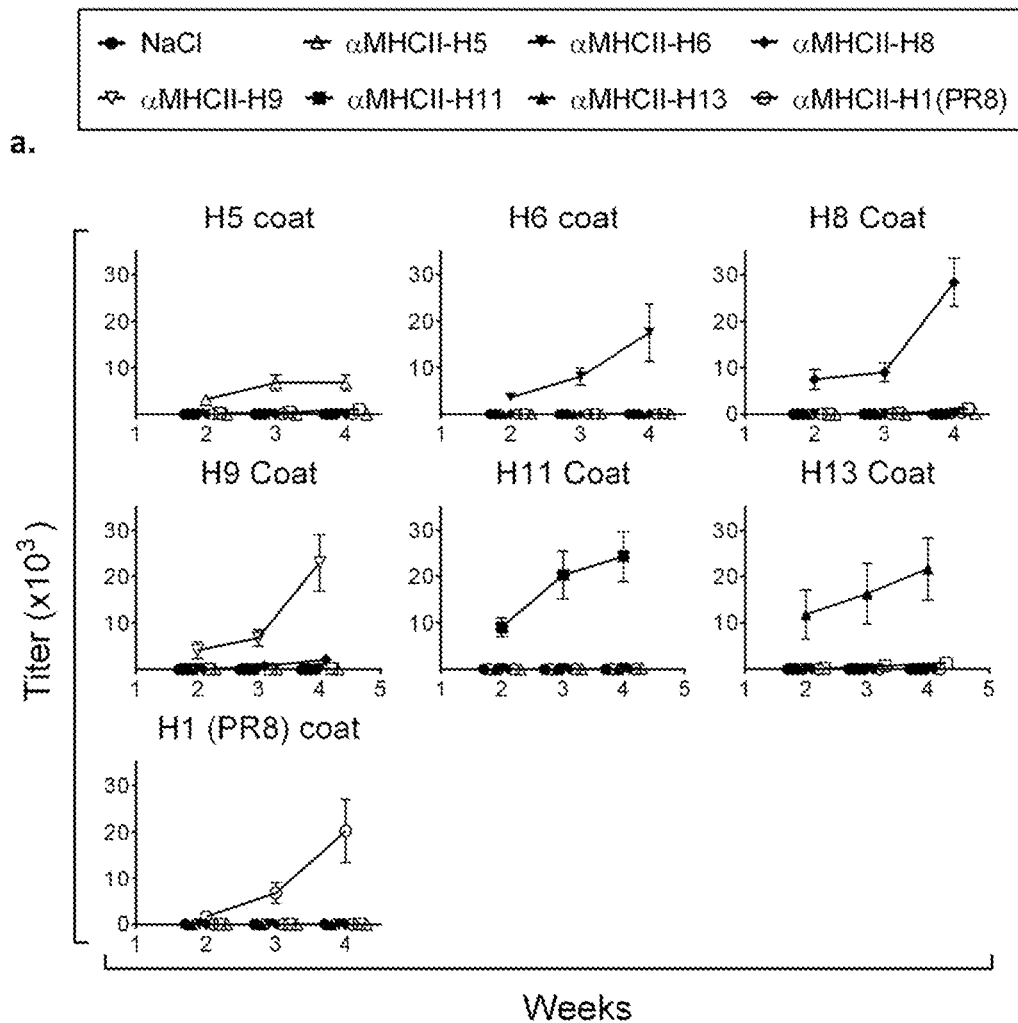
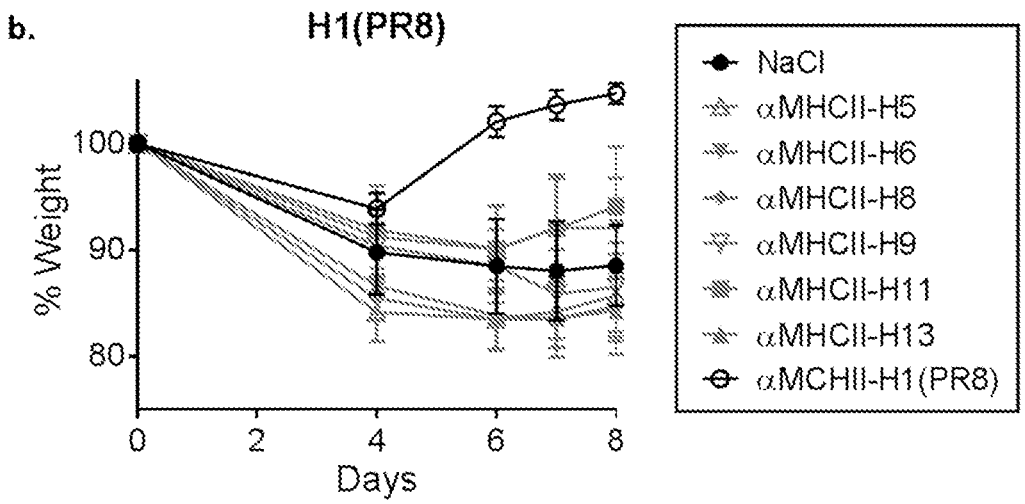

FIG. 6
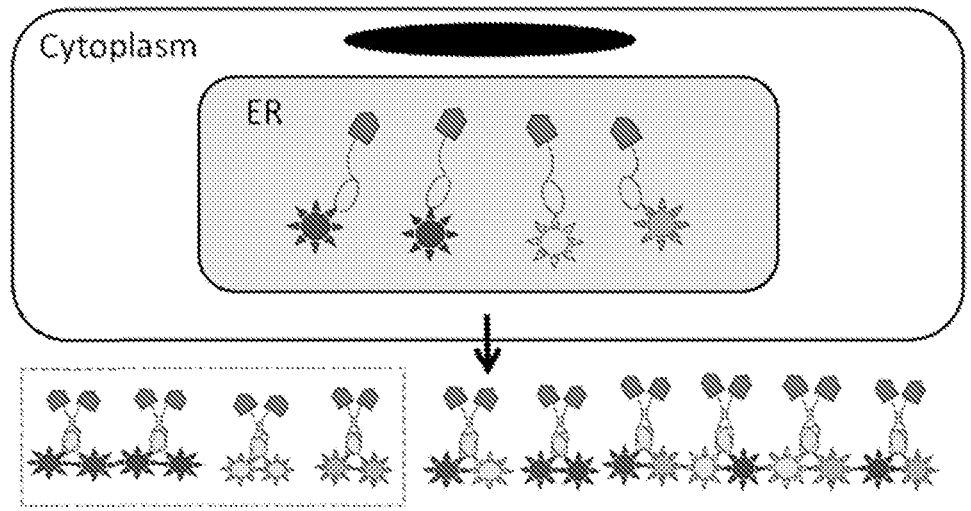
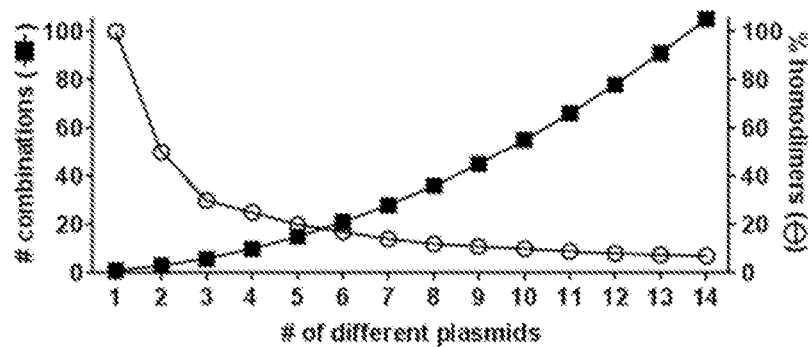

FIG. 7

```
                 18                                                                              97
(SEQ ID NO:15)PR8    DTICIGYHANNSTDTVDTVLEKNVTVTHSVNLLEDSHNGKLCRLKGIAPLQLGKCNIAGWLLGNPECDPLLPVRSWSYIV
(SEQ ID NO:16)Cal07  DTLCIGYHANNSTDTVDTVLEKNVTVTHSVNLLEDKHNGKLCKLRGVAPLHLGKCNIAGWILGNPECESLSTASSWSYIV
(SEQ ID NO:17)H5     DQICIGYHANNSTEQVDTIMEKNVTVTHAQDILERTHNGKLCDLNGVKPLILRDCSVAGWLLGNPMCDEFINVPEWSYIV
(SEQ ID NO:18)H6     DKICIGYHANNSTTQVDTILEKNVTVTHSVELLENQKEERFCKILNKAPLDLRGCTIEGWILGNPQCDLLLGDQSWSYIV
(SEQ ID NO:19)H8     DRICIGYQSNNSTDTVNTLIEQNVPVTQTMELVETEKHPAYCNTDLGAPLELRDCKIEAVIYGNPKCDIHLKDQGWSYIV
(SEQ ID NO:20)H9     DKICIGHQSTNSTETVDTLTETNVPVTHAKELLHTEINGMLCATSLGHPLILDTCTIEGLVYGNPSCDLLLGGRESWSYIV
(SEQ ID NO:21)H11    DEICIGYLSNNSTDKVDTIIENNVTVTSSVELVETEHTGSFCSINGKQPISLGDCSFAGWILGNPMCDDLIGKTSWSYIV
(SEQ ID NO:22)H13    DRICVGYLSTNSSERVDTLLENNVPVTSSVDLVETNHTGTYCSLGGISPVHLGDCSFEGWIVGNPACASNLGIRESYLI 98                                                                             173
PR8      ETPNSENGICYPGDFIDYEELREQLSSVSSFERFEIFPKESSWPNHN-TN-GVTAACSH-EGKSSFYRNLLWLTE-KEGS
Cal07    ETPSSDNGTCYPGDFIDYEELREQLSSVSSFERFEIFPKtSSWPNHD-SNKGVTAACPH-AGAKSFYKNLIWLVK-KGNS
H5       EKASPANDLCYPGNFNDYEELKHLLSRISHFEKIQIIPK-SSWSNHDaSS-GVSSACPY-LGKSSFFRNVVWLIK-KNST
H6       ERPTAQNGICYPGALNEVEELKALIGSGERVERFEMFPK-STWTGVD-TSsGVTKACPY-NSGSSFYRNLLWIIKTKSAA
H8       ERESAPEGMCYPGSIENLEELPFVFSSAASYKPIRLSDY-SRWNVTR-SG--TSKACNAsTGGQSFYRSINWLTKKKPDT
H9       ERSSAVNGTCPGNVENLEELRTLFSSASSYQRIQIPPD-TTWNVTY-TG--TSRACSG-----SFYPSMRWLTQKS-GF
H11      EKENPTNGICYPGILENEEELRLKFSGVLESNKFEASTS-NGWGAVN-SGaCSTAACKF-GSSNSFFRNMIWLIHQS-GT
H13      EDPSAPHGLCYPGELDNNGEIPHLFSGIRSFSRTELIAP-TSWGAVN-DG--VSSACQD-KGASSFYRNLVWFVERG-NK 174                                                                           253
PR8      YPKLKNSYVNKKGKEVLVLWGIHHPPNSKEQQNLYQNENAYVSVVTSNYNRRFTPEIAERPKVRDQAGRMNYYWTLLKPG
Cal07    YPKLSKSYINDKGKEVLVLWGIHHPSTSADQQSLYQNADAYVFVGSSRYSKKFKPEIAIRPKVRDQEGRMNYYWTLVEPG
H5       YPTIKRSYNNTNQEDLLVLWGIHHPNDAAEQTKLYQNPTTYISVGTSTLNQRLVPEIATPFKVNGQSGRIEFFWTILKPN
H6       YPVIKGTYNNTGSQPILYFWGVHHPPDTNEQNTLYGSGDRVVRMGTESMNFAKSPEIAARPAVNGQRGEIDYWSVLKPG
H8       YDFNEGTYVNNEDGDIIFLWGIHHPPDTKEQTTLYKNANTLTSVTTNTINPNFQPNIGPRPLVRGQQGRMDYYWGILKRG
H9       YPVQDAQYTNNRGKSILFVWGIHHPPTYTEQTNLYIRNDTTTSVTTEDLNRTFKPVIGPRPLVNLQLGPIDYWSVLKPG
H11      YPVIKRTFNNTKGRDVLVVWGIHHPATLKEHQDLYKKDSSYVAVGSETYNRRFTPEISTREKVNGQAGRMTFYWTIVKPG
H13      YPVIRGTYNNTTGRDVLVIWGIHHPVSTDEARKLYVNDNPYTLVSTSSWSRKYNLEIGIPEGYNGQKSWMKIYWYLMHPG 254                                                                           331
PR8      DTIIFEANGNLIAPMYAFA-LSRGFGSGIITS-NASMHECNTKCQTPLGAINSSLPYQNIHPVTIGECPKYVRSAKLRMV
Cal07    DKITFEATGNLVVPRYAFA-MERNAGSGIIIS-DTPVHDCNTKCQTPKGAINTSLPFQNIHPITIGKCPKYVKSTKLRLA
H5       DAINFESNGNFIAPEYAYK-IVKKGDSTIMKS-ELEYGNCNTKCQTPMGAINSSMPFHNIHPLTIGECPKYVRSNRLVLA
H6       ETLNVESNGNLIAPWYAYK-FVSTNNKGAIFKS-NLPIENCDATCQTIAGVLRTNKTFQNVSPLWIGECPKYVKSESLRLA
H8       ETLKIRTNGNLIAPEFGYL-LKGESHGRIIQNeDIPIGNCNTKCQTPTYACAINSSKPFQNASRHYMGECPKYVKKASLRLA
H9       QTLRVRSNGNLIAFWYGHV-LSGGSHCGRILKT-DLKGGNCVVQCQTEKGGLNSTLPFHNISKYAFGTCPKYVRVNSLKLA
H11      ESITFESNGAFLAPRYAFE-IVSVGNGKLFRS-ELNIESCSTKCQTEVGGINTNKSFHSVHRNTIGDCPKYVNVKSLKLA
H13      ESISPESNGGLLAFKYGYI-IEEYGKCRIFQS-RIRIAKCNTKCQTSVGGINTNKTFQNIERNALGDCPKYIKSGQLKLA

332           HA1 --- HA2                                                     411
PR8      TGLRNIPSIQSRGLFGAIAGFIEGGWTGMIDGWYGYHHQNEQGSGYAADQKSTQNAINGITNKVNTVIEKMNIQFTAVGK
Cal07    TGLRNIPSIQSRGLFGAIAGFIEGGWTGMVDGWYGYHHQNEQGSGYAADLKSTQNAIDEITNKVNSVIEKMNTQFTAVGK
H5       TGLRNAPQREKRGLFGAIAGFIEGGWQGMVDGWYGYHHSNEQGSGYAADQESTQKAIDGVTNKVNSIINKRNTQFEAVGK
H6       TGLRNVPQIETRGLFGAIAGFIEGGWTGMIDGWYGYHHENSGSGYAADKESTQKAIDGITNKVNSIIDKMNTQFEAVDH
H8       VGLRNTPSVEPRGLFGAIAGFIEGGWSGMIDGWYGFHHQNSEGTGMAADQKSTQEAIDKITNKVRNNIVDKMNREFEVVNH
H9       VGLRNVPARSSPGLFGAIAGFIEGGWPCLVAGWYGFQHSNDQGVGMAADRDSTQKAIDKITSEVNNIVDKMNKQYEIIDH
H11      TGLRNVPAIASKGLFGAIAGFIEGGWPGLINCWYGFQHRNEEGTGIAADKESTQKAIDQITSKVNNIVDRMNTNPESVQH
H13      TGLRNVPAISKPGLFGAIAGFIEGGWPGLINGWYGFQHQREQGVGMAADKESTQKAIDQITTEINNIIEKMNGNYDSIRG
                                         B
                                       CD4+T 412                                                                           491
PR8      EFNKLEKRPMENLNKKVDDGFLDIWTYNAELLVLLENERTLDFHDSNVKNLYEKVKSQLKNNAKEIGNGCFEFYHKCDNEC
Cal07    EFNHLEKRIENLNKKVDDGFLDIWTYNAELLVLLENERTLDYHDSNVKNLYEKVRSQLKNNAKEIGNGCFEFYHKCDNTC
H5       EFNNLERRIENLNKKMEDGFLDVWTYNAELLVLMENERTLDFHDSNVRNLYDKVRLQLRDNAKELGNGCFEFYHKCDNEC
H6       EFSNLERRIDNLNKRMEDGFLDVWTYNAELLVLLENERTLDLHDANVRNLYEKVKSQLRDNANDLGNGCFEFWEKCDNEC
H8       EFSEVEKRINMIRDKIDDQIEDLWAYNAELLVLLENQKTLDEHDSNVKNLFDEVKRRLSANAIDAGHGCFDILHKCDNEC
H9       EFSEVETRLNMINNNKIDDQIQSVWAYNAELLVLLENQKTLDEHDANVNNLYNKVKRALGSNAMEDGKGCFELYHKCDDQC
H11      EFSEIEERINRLSKHVDSVVDIWSYNAQLLVLLENEKTLDLHDSNVRNLHERVRRMLKDNAKDECHGCFTFYHKCDNEC
H13      EFSQVEQRINMLADRIDDAVTQVWSYNAKLLVLLENDKTLDMHDANVRNLHDQVRRVLKTNAIDEGNGCFELLHKCNDSC
                                                                               CD4+T 492                                                           541
PR8      MESVRNGTYDYPKYSEESKLNPEKVDGVKLESMG-IYQILAIYSTVASSL
Cal07    MESVKNGTYDYPKYSEEAKLNREEIDGVKLESTR-IKQLAIYSTVASSL
H5       MESVKNGTYDYPQYSEEARLNREEISGVKLESMG-TYQ-----------
H6       IESVKNGTYDYPKYQDESKLNRQEIESVKIDNLG-VIQILAIYSTVSSSL
H8       METIKNGTYNHKEYEEEAKLERSKINGVKLEENT-TYKILSIYSTVAASL
H9       METIRNGTYNRRKYREESRLEFQKIEGVKLESEG-TYKILTIYSTVASSL

H11      IEKVRNGTYDHKEFEKESKINRQEIEGVKLDSSGnVYKILSIYSCIASSL
H13      METIRNGTYNHTEYEEESKLKPQEIEGIKLKSDDsVYKALSIYSCIASSI
                                                  CD8+
```

VACCINE MOLECULES

FIELD OF INVENTION

Provided herein is technology relating to vaccines and particularly, but not exclusively, to compositions, methods, and uses of a mixture of immunogenic vaccine molecules comprising components for targeting the dimeric vaccine molecules to antigen-presenting cells and components for eliciting an immunogenic response, wherein the components for eliciting an immunogenic response preferably comprise at least three variants of an immunogenic protein, such as variants of immunogenic proteins obtained from three or more different strains of a pathogenic organism.

BACKGROUND

Influenza viruses are constantly evolving, thus evading the potential neutralization by antibodies formed during previous virus exposures. The evolution is mostly driven by antigenic drift, where non-synonymous point mutations induced during virus replication cause amino acid changes that abrogate recognition by neutralizing antibodies. On a more sporadic basis, more drastic antigenic shifts may occur due to genetic reassortments, potentially causing outbreaks of pandemic influenza. Until today, the major causes of influenza-related morbidity and mortality in humans have been the H1, H2 and H3 subtypes of influenza A, as illustrated by the three pandemics of the $20^{th}$ century: the 1919 Spanish flu (H1), the 1957 Asian flu (H2) and the 1968 Hong Kong flu (H3). However, recently emerging subtypes of traditionally zoonotic (primarily avian) strains such as H5, H6, H7, H9 and H10 influenzas have caused severe but isolated disease outbreaks in humans (1-5), and may possibly cause future influenza pandemics. Since current vaccines predominantly induce strain specific antibodies (6, 7), and require a substantial amount of time for production (8-10), novel vaccine strategies conferring broader protection are needed.

DNA vaccines are currently in vogue due to their potential for rapid insertion of novel antigens, and a speedy vaccine production. However, DNA vaccines are typically hampered by low immunogenicity, particularly in larger animals and humans. In order to remedy this shortcoming, better methods of DNA delivery have been developed (11-13). However, the improvements have typically been restricted to more efficient DNA uptake by cells at the site of delivery. In another strategy, DNA has been so constructed that it encodes secreted fusion proteins that target antigen to antigen presenting cells (APC) for enhanced immune responses (14-19). This approach combines the attractiveness of DNA immunization with the well-known principle of APC-targeting of antigen to increase antigen immunogenicity (20-22). Interestingly, targeting of antigen to different APC surface molecules may skew immune responses towards different arms of immunity (17, 23, 24). Thus, the technology may allow matching of vaccine-induced immune responses to the type of immunity needed for protection against a particular pathogen.

SUMMARY

There is a need for development of vaccines that can confer broad immunity against highly diverse pathogens such as influenza. The efficacy of conventional influenza vaccines is dependent on accurate matching of vaccines to circulating strains, but slow and limited production capacities increase the probability of vaccine mismatches. By contrast, DNA vaccination allows for rapid production of vaccines encoding novel influenza antigens. The efficacy of DNA vaccination is greatly improved if the DNA-encoded vaccine proteins target antigen presenting cells (APC). Here, hemagglutinin (HA) genes from each of six group 1 influenza viruses (H5, H6, H8, H9, H11, H13) were inserted into a DNA vaccine format that induce deliverance of the HA protein antigens to major histocompatibility complex (MHC) class II molecules on APC. Each of the targeted DNA vaccines induced high titers of strain-specific anti-HA antibodies. Importantly, when the six different HA vaccines were mixed and injected simultaneously, the strain-specific antibody titers were maintained. In addition, the vaccine mixture induced antibodies that cross-reacted with strains not included in the vaccine mixture (H1), and could protect mice against a heterosubtypic challenge with the H1 viruses PR8 and Cal07. The data suggest that vaccination with a mixture of various HAs could be useful for induction of strain-specific immunity against strains represented in the mixture, and in addition confer some degree of cross-protection against unrelated influenza strains.

Current influenza vaccines are hampered with respect to efficacy and a prolonged production time. Described herein is a vaccine concept where, for example, six hemagglutinins (HAs) from different influenza subtypes are mixed together with the aim of inducing strong antibody responses against each of these HAs. For increased efficacy, the HAs were targeted towards major histocompatibility complex (MHC) class II molecules expressed on antigen presenting cells. Importantly, one could also demonstrate that vaccination with this HA mixture conferred protection against an influenza subtype not included in the vaccine. Presumably, conserved epitopes will become more visible to the immune system in such a mixture, since strain specific epitopes are more diluted. Thus, described herein is a strategy by which strong antibody responses could be generated against the most relevant influenza strains, and in addition confer basic protection in the event of an unforeseen antigenic shift.

Accordingly, in some embodiments, the present invention provides a DNA vaccine comprising three or more different nucleic acid constructs, each of the constructs encoding a fusion protein comprising a targeting unit, a multimerization domain, and an antigenic unit in operable association, wherein the antigenic unit for each of the three or more different nucleic acid constructs differ by encoding different variant target antigenic proteins and wherein when the three or more different nucleic acid constructs are introduced into a cells a random mixture of multimeric protein molecules comprising the same and different variant target antigenic proteins are produced via association of the multimerization domains. In some embodiments, multimers are dimers and the multimerization domain is a dimerization domain.

In some embodiments, the multimerization domain is a hinge/$C_H3$ dimerization domain. In some embodiments, the targeting unit is an antigen binding protein. In some embodiments, the antigen binding protein is an scFv. In some embodiments, the targeting unit is an Antigen Presenting Cell (APC) targeting unit. In some embodiments, the APC targeting unit binds to a target selected from the group consisting of MHC-II molecules, CD40, CD14, HLA-DP, Toll-like receptors, and chemokine receptors.

In some embodiments, the different variant antigenic target proteins have greater than about 30%, 40%, 50%, 60%, 70%, 80%, 90% or 95% sequence identity. In some embodiments, the different variant antigenic target proteins are from different strains of an organism. In some embodiments, the organism is a pathogenic organism. In some embodiments, the organism is selected from the group consisting of a virus, a bacterium, a fungus and a protozoan. In some embodiments, the different variant antigenic target proteins are variants of hemagglutinin (HA). In some embodiments, the vaccine comprises variants of HA from at least three, four, five or six strains of influenza viruses. In some embodiments, the influenza viruses are group 1 influenza viruses. In some embodiments, the group 1 influenza viruses are selected from the group consisting of H5, H6, H8, H9, H11, and H13. In some embodiments, the different variant antigenic target proteins are variants of a cancer antigen.

In some embodiments, the random mixture of dimeric protein molecules comprises a defined number of different dimeric molecules, where the defined number of different dimeric molecules is calculated by the formula $[n(n+1)]/2$ where n is the number of different variant antigenic target proteins. In some embodiments, the number of different dimeric molecules is 6 when n is 3, 10 when n is 4, 15 when is n 5 and 21 when n is 6.

In some embodiments, the sequence encoding the fusion protein is operably linked to a promoter, preferably an exogenous promoter.

In some embodiments, the present invention provides a vaccine composition comprising a mixture of multerimeric, preferably dimeric protein molecules, wherein the mixture of multimeric protein molecules comprise a mixture of at least 3 different fusion protein monomers comprising a targeting unit, a multimerization domain, and an antigenic unit in operable association, wherein the antigenic unit for each of the three different fusion protein monomers differ by encoding different variant target antigenic proteins, and wherein the multimeric protein molecules comprise two of the monomers joined by association of the multimerization domains.

In some embodiments, the multimers are dimers and the multimerization domain is a dimerization domain.

In some embodiments, the dimerization domain is a hinge/$C_H3$ dimerization domain. In some embodiments, the targeting unit is an antigen binding protein. In some embodiments, the antigen binding protein is an scFv. In some embodiments, the targeting unit is an Antigen Presenting Cell (APC) targeting unit. In some embodiments, the APC targeting unit binds to a target selected from the group consisting of MHC-II molecules, CD40, CD14, HLA-DP, Toll-like receptors, and chemokine receptors.

In some embodiments, the different variant antigenic target proteins have greater than about 30%, 40%, 50%, 60%, 70%, 80%, 90% or 95% sequence identity. In some embodiments, the different variant antigenic target proteins are from different strains of an organism. In some embodiments, the organism is a pathogenic organism. In some embodiments, the organism is selected from the group consisting of a virus, a bacterium, a fungus and a protozoan. In some embodiments, the different variant antigenic target proteins are variants of hemagglutinin (HA). In some embodiments, the vaccine comprises variants of HA from at least three, four, five or six strains of influenza viruses. In some embodiments, the influenza viruses are group 1 influenza viruses. In some embodiments, the group 1 influenza viruses are selected from the group consisting of H5, H6, H8, H9, H11, and H13. In some embodiments, the different variant antigenic target proteins are variants of a cancer antigen.

In some embodiments, the random mixture of dimeric protein molecules comprises a defined number of different dimeric molecules, where the defined number of different dimeric molecules is calculated by the formula $[n(n+1)]/2$ where n is the number of different variant antigenic target proteins. In some embodiments, the number of different dimeric molecules is 6 when n is 3, 10 when n is 4, 15 when is n 5 and 21 when n is 6.

In some embodiments, the present invention provides a pharmaceutical formulation comprising the DNA vaccine or vaccine composition as described above and a pharmaceutically acceptable carrier.

In some embodiments, the present invention provides a vaccine formulation comprising a vaccine composition as described above and an adjuvant.

In some embodiments, the present invention provides a method of immunizing or inducing an immune response to variant target antigenic proteins in a subject comprising administering to the subject a DNA vaccine, vaccine composition, pharmaceutical formulation or vaccine formulation as described above to a subject.

In some embodiments, the present invention provides for use of a DNA vaccine, vaccine composition, pharmaceutical formulation or vaccine formulation as described above to immunize or induce an immune response in a subject in need thereof.

In some embodiments, the present invention provides for use of a DNA vaccine, vaccine composition, pharmaceutical formulation or vaccine formulation as described above as a vaccine to prevent or to treat infection by a pathogen.

In some embodiments, the present invention provides for use of a DNA vaccine, vaccine composition, pharmaceutical formulation or vaccine formulation as described above as a vaccine to prevent or to treat cancer.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

Figure 1:
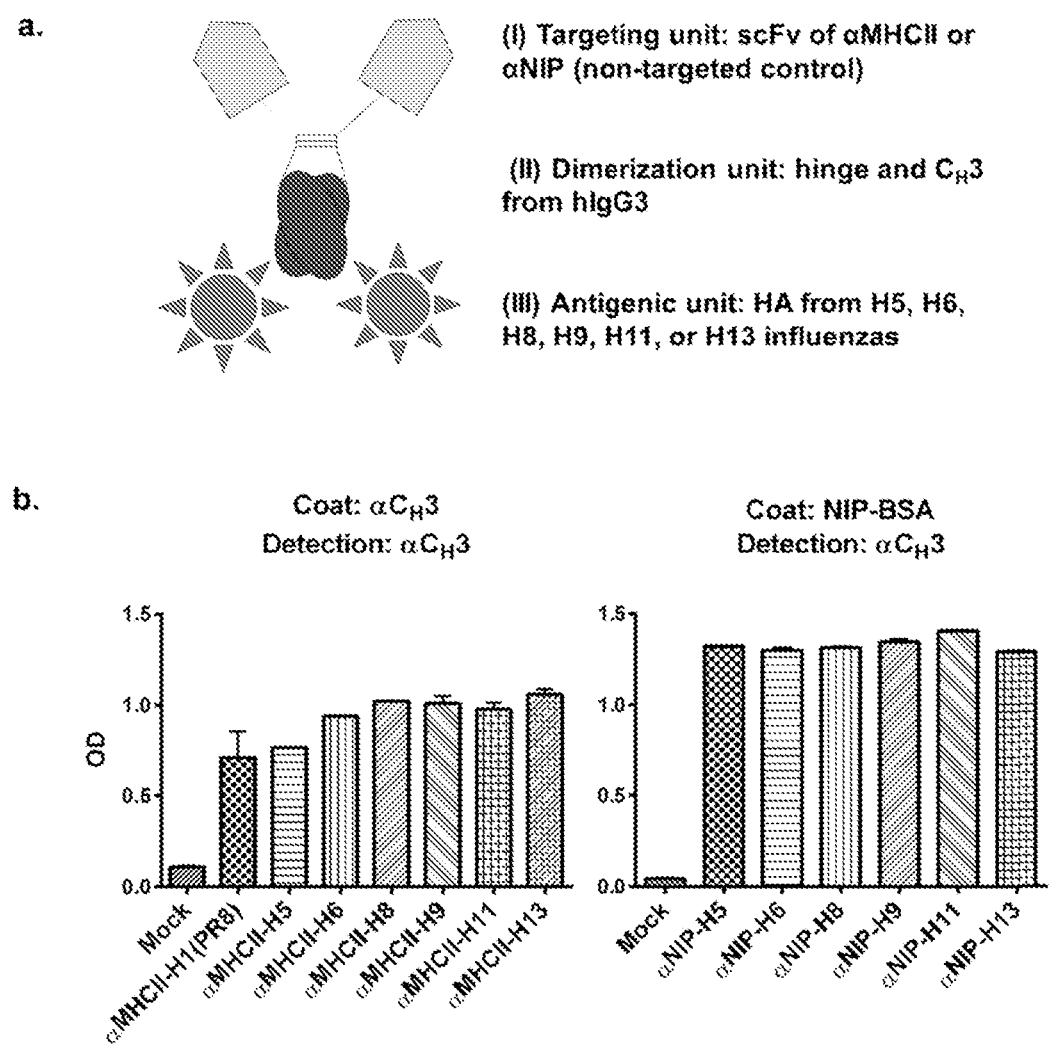

FIG. 1: Characterization of vaccine proteins. (a) The MHCII-targeted vaccine proteins consist of (i) a targeting unit (scFv) that is specific for MHC class II, (ii) a dimerization unit containing a shortened hinge and $C_H3$ from human γ3, and (iii) an antigenic unit encoding one of the six indicated HAs. Non-targeted controls have been prepared by replacement of the targeting unit with a scFv that is specific for the hapten NIP. (b) Supernatants from HEK293E cells transfected with the DNA plasmids encoding the indicated vaccines were analyzed in sandwich ELISAs. An MHCII-targeted vaccine encoding HA from PR8 (αMHCII-H1) was included as positive control.

FIG. 2: High strain specific IgG titers after a single MHCII-targeted vaccination. BALB/c mice (n=6/group) were immunized once with 25 μg plasmids encoding one of the indicated vaccines. (a) Sera were harvested at weeks 2, 3 and 4 after vaccination, and IgG responses in sera from each of the vaccine groups measured by ELISAs against recombinant HA from H5, H6, H8, H9, H11, H13 and H1 (PR8) influenzas (mean+/−SEM). (b) Four weeks after a single immunization, all mice were challenged with a lethal dose of influenza PR8 (H1N1), and monitored for weight loss.

FIG. 3: Antibody responses against all included HAs after DNA immunization with vaccine mixtures. BALB/c mice (n=6/group) were immunized thrice (weeks 0, 4, 12) with 25

μg DNA of the indicated vaccine. Serum samples were harvested 2-3 weeks after each vaccine delivery, and HA specific IgG responses measured in sandwich ELISAs against recombinant HA from H5, H6, H8, H9, H11 and H13 influenzas (mean+/−SEM). p-values (two-way Anova) were calculated for αMHCII-MIX vs αNIP-MIX at the different time points and marked as follows: *p<0.05 (*), p<0,01, and *p<0.001.

Figure 4:
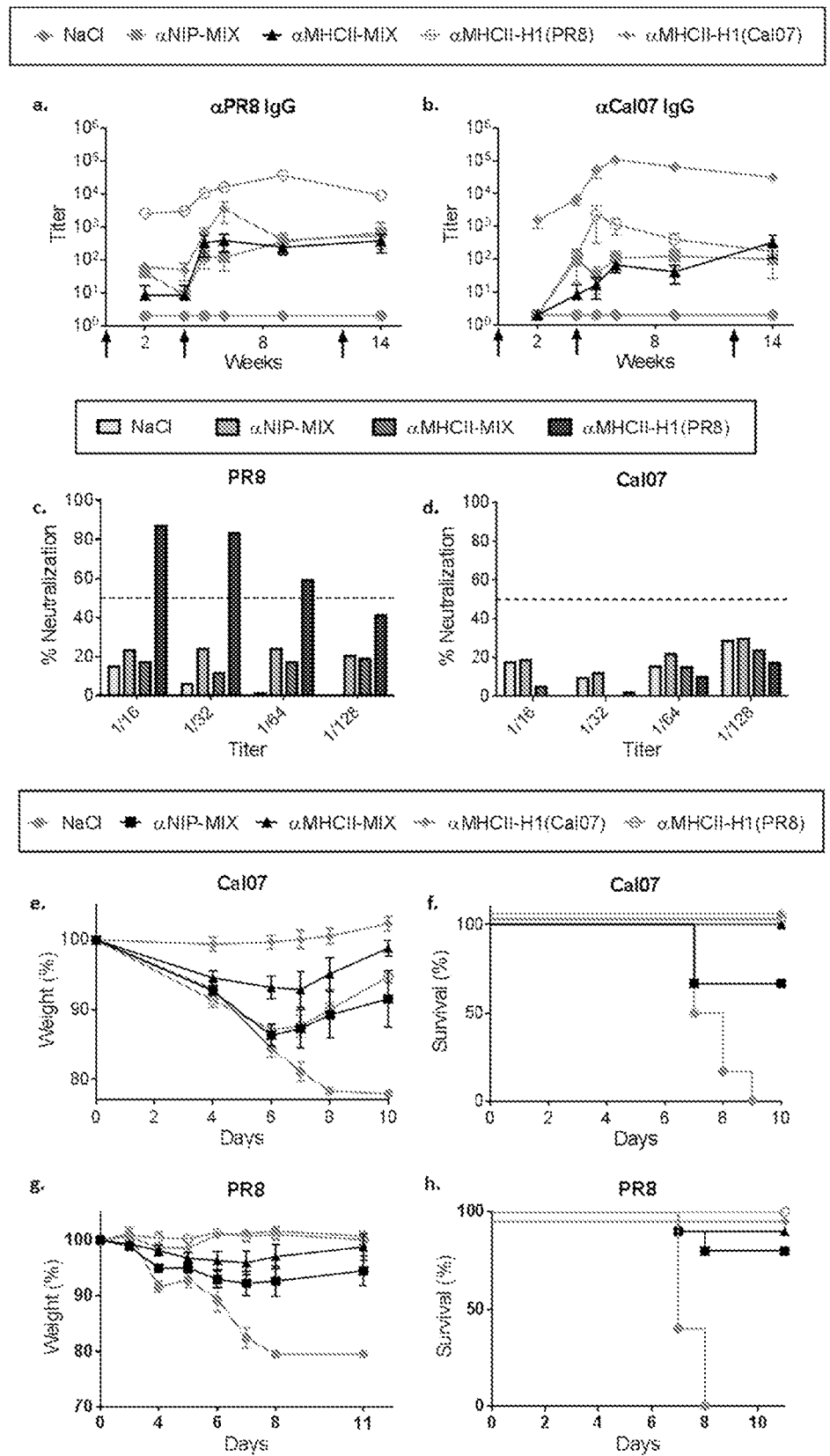

FIG. 4: Vaccination with αMHCII-MIX confers heterosubtypic protection against H1-influenza viruses not included in the vaccine mixture. (a-b) BALB/c mice (n=6/group) were immunized thrice (weeks 0, 4, 12, as indicated by arrows) with 25 μg DNA/EP of the indicated vaccines, and serum IgG measured against PR8 (a) or Cal07 (b) in ELISAs (mean+/−SEM). (c-d) Micro-neutralization assays were performed on sera harvested two weeks after the third vaccination with PR8 (c) and Cal07 (d), respectively. Dotted line indicates 50% threshold for positive neutralization. (e-f) Two weeks after the third vaccination (above), mice were challenged with a lethal dose of Cal07 and monitored for weight loss (+/−SEM) (e) and survival (f). (g-h) In a new experiment, mice were vaccinated weeks 0, 4, and 12 (as above), and challenged with a lethal dose of influenza PR8 2 weeks after the third vaccination (n=10/group (black) or n=6/group (grey)). Mice were monitored for weight loss (+/−SEM (g) and survival (h).

Figure 5:
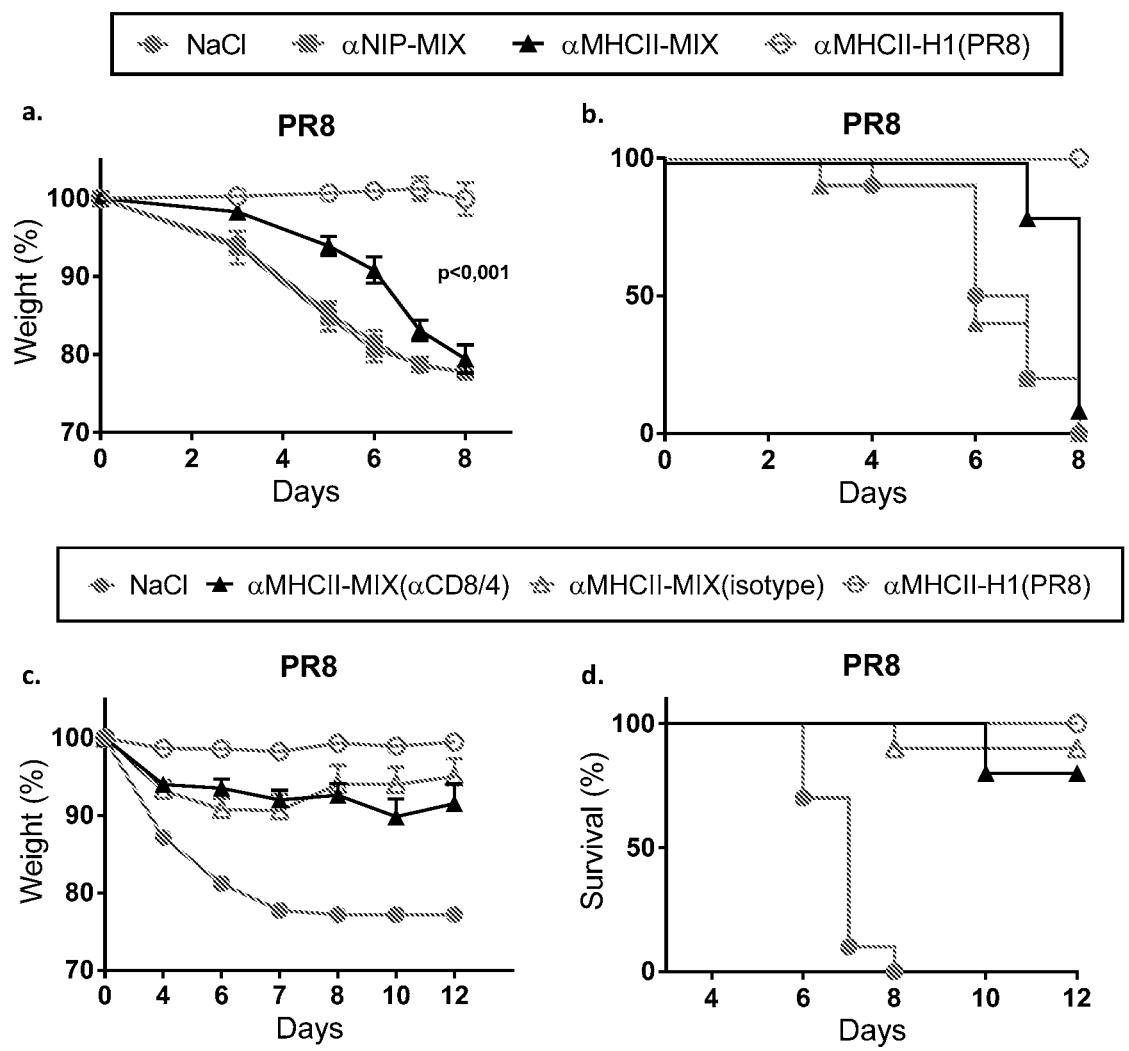

FIG. 5: Heterosubtypic protection against H1-virus by αMHCII-MIX vaccination is independent of T-cells. (a-b) BALB/c mice (n=7/group) were immunized thrice (week 0, 4 and 7) with 25 μg DNA/EP of the indicated vaccines. Sera from mice of each group were harvested 2 weeks after the third delivery, and transferred i.v. to naïve mice (n=10/group) before a lethal challenge with PR8. Mice were monitored for weight loss (a) and survival (b). The results are representative for two independent experiments. (c-d) BALB/c mice (n=10) were immunized thrice (week 0, 4, 7) with 25 μg DNA/EP of the indicated vaccines, and then injected every other day from day 12 after the third vaccination with depleting mAbs against CD4 and CD8 T-cells, or isotype matched control mAbs. A lethal dose of PR8 was administered at day 14, and the mice monitored for (c) weight loss and (d) survival. Efficient depletion was confirmed by staining of splenocytes (S5).

FIG. 6: Random dimerization of vaccine monomers in the ER. (a) Following co-transfections of DNA plasmids into a single cell, monomeric peptide chains containing a particular HA will dimerize randomly in the ER. Thus, the secreted dimeric vaccine proteins may display either two identical or two different subtypes of HA. (b) The number of possible dimeric combinations will increase rapidly with increasing number of plasmids included in the mixture. The relationship is given by (n(n+1))/2.

FIG. 7: Sequence alignments. Alignments were made using the NCBI Basic Logical Alignment Search Tool (BLAST). Amino acids that are conserved in at least 5 of the selected strains are marked with red. Known conserved B- and T-cell epitopes are underlined. Top row numbering is according to PR8.

Figure 8:
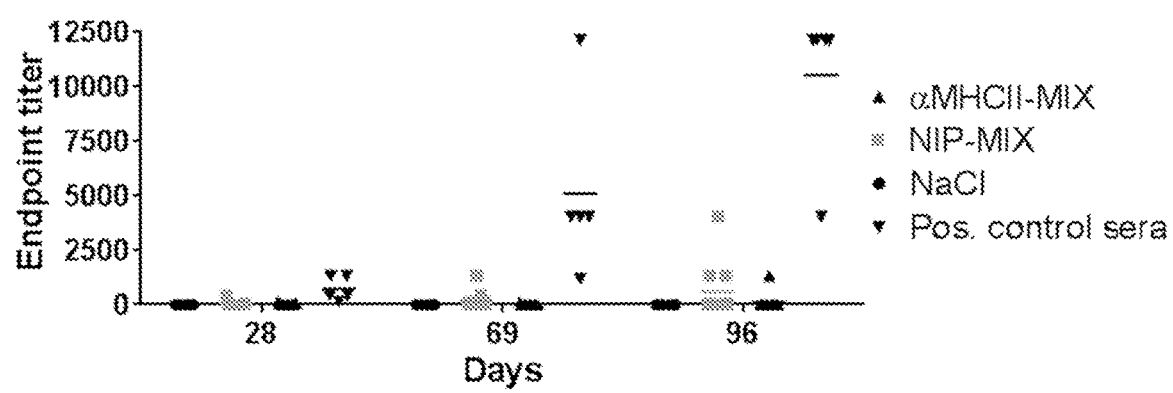

FIG. 8: Induction of stem reactive antibodies in sera. BALB/c mice [n=6 (NaCl), or 10/group] were immunized thrice (week 0, 4 and 7) with 25 μg DNA/EP of the indicated vaccines. An ELISA coated with Phox-BSA, and then recombinant proteins expressing Phox-specific scFv which was linked, via an irrelevant dimerization unit, to the HA stem, was used to measure HA stem-specific IgG. Responses are given for individual mice, with the mean indicated.

Figure 9:
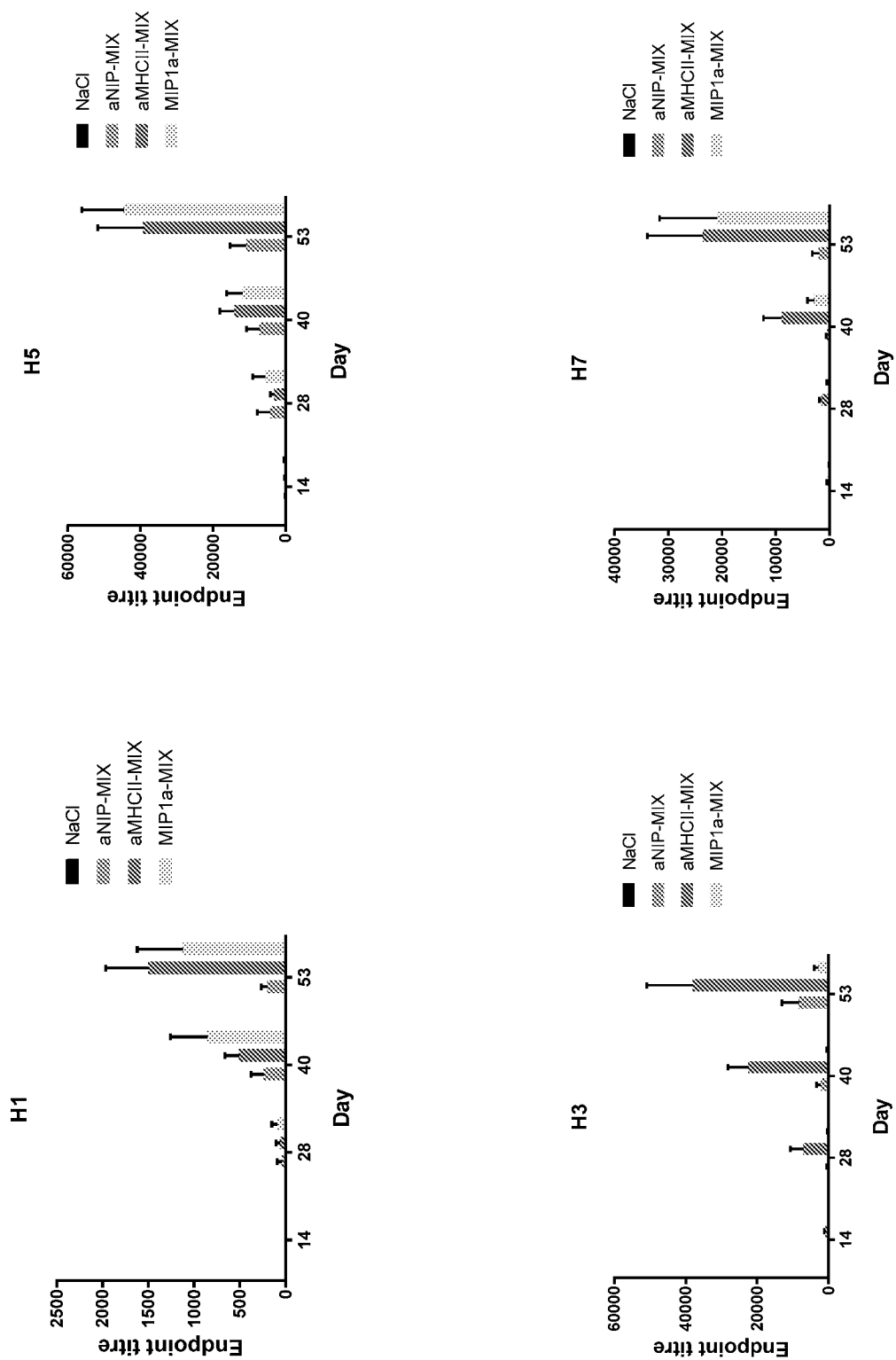

FIG. 9: Immunization with subtype mixtures. Antibody responses monitored longitudinally by ELISA against recombinant HA proteins from influenza H1 [A/PR/8/1934 (H1N1)], H5 [A/Hong Kong/483/97 (H5N1)], H3 [A/Hong Kong/1/1968 (H3N2)], or H7 [A/Shanghai/1/2013 (H7N9)].

Figure 10:
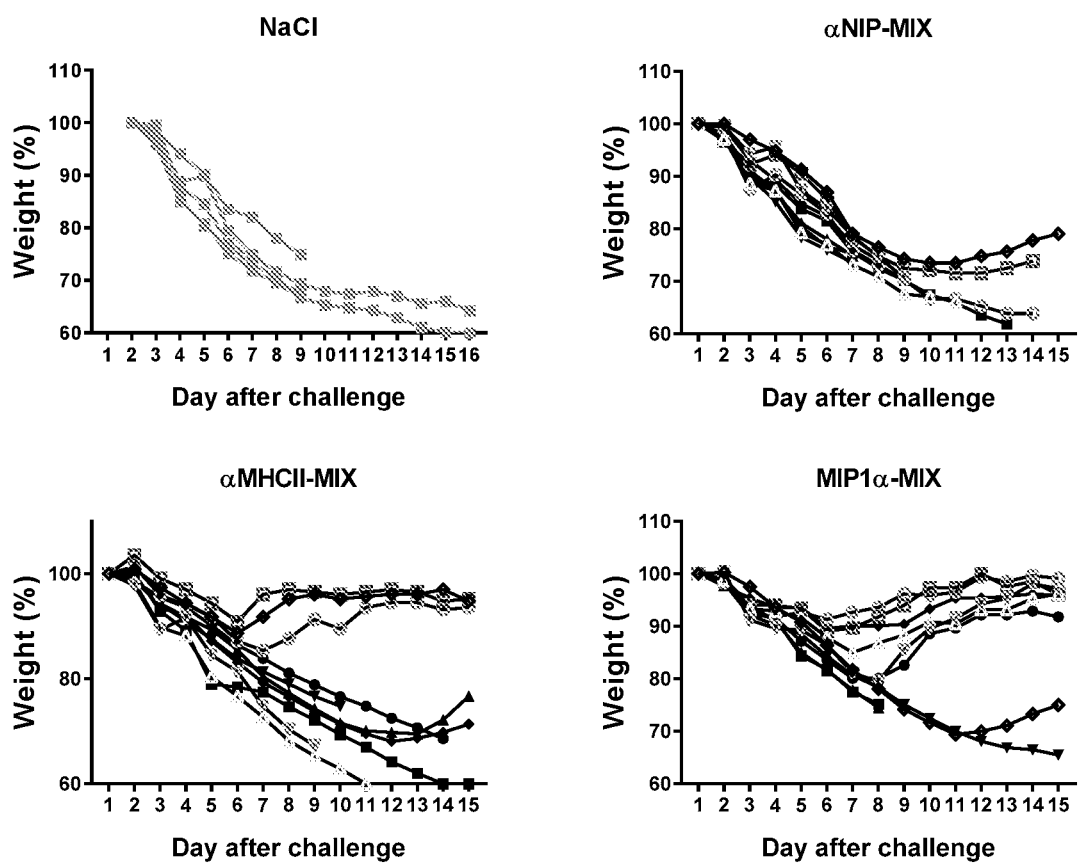

FIG. 10: APC targeted immunization. Weight loss of mice after immunization with the indicated mixtures and challenge with influenza A/PR/8/1934 (H1N1) (2.5LD50).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to vaccines and particularly, but not exclusively, to compositions, methods, and uses of a mixture of immunogenic vaccine molecules comprising components for targeting multimeric (e.g., dimeric) vaccine molecules to antigen-presenting cells and components for eliciting an immunogenic response, wherein the components for eliciting an immunogenic response preferably comprise at least three variants of an immunogenic protein, such as variants of immunogenic proteins obtained from three or more different strains of a pathogenic organism.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "subject" and "patient" refer to any animal, such as a mammal like a dog, cat, bird, livestock, and preferably a human.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (e.g., minimize or lessen) the targeted pathologic condition or disorder. Those in need of treatment include those already with the disorder as well as those prone to have the disorder or those in whom the disorder is to be prevented.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F'(ab)$_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments.

A molecule that "specifically binds to" or is "specific for" another molecule is one that binds to that particular molecule without substantially binding to any other molecule.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the term "administration" refers to the act of giving a drug, prodrug, antibody, vaccine, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, "carriers" include pharmaceutically acceptable carriers, excipients, or stabilizers which are nontoxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants.

As used herein, the terms "protein," "polypeptide," and "peptide" refer to a molecule comprising amino acids joined via peptide bonds. In general, "peptide" is used to refer to a sequence of 20 or less amino acids and "polypeptide" is used to refer to a sequence of greater than 20 amino acids.

As used herein, the term, "synthetic polypeptide," "synthetic peptide", and "synthetic protein" refer to peptides, polypeptides, and proteins that are produced by a recombinant process (i.e., expression of exogenous nucleic acid encoding the peptide, polypeptide, or protein in an organism, host cell, or cell-free system) or by chemical synthesis.

As used herein, the term "protein of interest" refers to a protein encoded by a nucleic acid of interest.

As used herein, the term "native" (or wild type) when used in reference to a protein refers to proteins encoded by the genome of a cell, tissue, or organism, other than one manipulated to produce synthetic proteins.

As used herein, "domain" (typically a sequence of three or more, generally 5 or 7 or more amino acids) refers to a portion of a molecule, such as proteins or the encoding nucleic acids, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as proteolytic activity. As such, a domain refers to a folded protein structure that retains its tertiary structure independently of the rest of the protein. Generally, domains are responsible for discrete functional properties of proteins, and in many cases may be added, removed or transferred to other proteins without loss of function of the remainder of the protein and/or of the domain.

A protein can have one, or more than one, distinct domains. For example, a domain can be identified, defined or distinguished by homology of the sequence therein to related family members, such as homology to motifs that define a protease domain or a gla domain. In another example, a domain can be distinguished by its function, such as by proteolytic activity, or an ability to interact with a biomolecule, such as DNA binding, ligand binding, and dimerization. A domain independently can exhibit a biological function or activity such that the domain independently or fused to another molecule can perform an activity, such as, for example proteolytic activity or ligand binding. A domain can be a linear sequence of amino acids or a non-linear sequence of amino acids. Many polypeptides contain a plurality of domains. Some domains are known and can be identified by those of skill in the art. It is to be understood that it is well within the skill in the art to recognize particular domains by name. If needed, appropriate software can be employed to identify domains.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism). The term "host cell" refers to any cell capable of replicating and/or transcribing and/or translating a heterologous gene. Thus, a "host cell" refers to any eukaryotic or prokaryotic cell, whether located in vitro or in vivo. For example, host cells may be located in a transgenic animal.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid or polypeptide or protein refers to a nucleic acid or polypeptide or protein sequence that is identified and separated from at least one contaminant nucleic acid or polypeptide or protein with which it is ordinarily associated in its natural source. Isolated nucleic acids or polypeptides or proteins are molecules present in a form or setting that is different from that in which they are found in nature. In contrast, non-isolated nucleic acids or polypeptides or proteins are found in the state in which they exist in nature.

The term "antigen" refers to a molecule (e.g., a protein, glycoprotein, lipoprotein, lipid, nucleic acid, or other substance) that is reactive with an antibody specific for a portion of the molecule.

The term "antigenic determinant" refers to that portion of an antigen that makes contact with a particular antibody (e.g., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (e.g., the "immunogen" used to elicit the immune response) for binding to an antibody.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

As used herein, a "vaccine" comprises one or more immunogenic antigens intentionally administered to induce acquired immunity in the recipient (e.g., a subject).

Embodiments of the Technology

Previously, it has been demonstrated that a single DNA immunization that causes targeting of influenza hemagglutinin (HA) to major histocompatibility complex class II (MHCII) molecules can confer long lasting antibody mediated protection against homotypic influenza challenges in mice (16). The increased efficacy conferred by MHCII-targeting of antigen has recently been translated to influenza vaccination of larger animals (19). As a mechanism for enhanced antibody induction, it has been suggested that the DNA-encoded αMHCII-HA vaccine proteins bridge B cells and APC in an APC-B cell synapse (14, 25, 26). Here, it is shown that the same MHCII-targeted DNA vaccine format can induce strong antibody responses against H5, H6, H8, H9, H11 or H13 subtypes of group 1 influenza viruses. It is further demonstrated that the strong antibody responses are maintained after delivery of a mixture containing the six DNA constructs within a single bolus. Importantly, the mixture containing the six different HAs could also induce cross-protective antibodies against group 1 strains of influenza that had not been included in the vaccination mix [A/PR/8/34 (H1N1) (PR8) and A/California/07/2009 (H1N1) (Cal07)].

Although the disclosure herein refers to certain illustrated embodiments, it is to be understood that these embodiments are presented by way of example and not by way of limitation.

In some embodiments, the present invention provides a DNA vaccine comprising three or more different nucleic acid constructs, each of said constructs encoding a fusion protein comprising a targeting unit, a multimerization domain, preferably a dimerization domain, and an antigenic unit in operable association. In some preferred embodiments, the antigenic units for each of the three or more different nucleic acid constructs differ by encoding different variant target antigenic proteins so that when the three or more different nucleic acid constructs are introduced into a cell a random mixture of multimeric (e.g., dimeric) protein molecules comprising the same and different variant target antigenic proteins are produced via association of the multimerization (e.g., dimerization) domains. This is shown schematically in FIG. 6. As can be seen in FIG. 6, introduction of the vaccine nucleic acid constructs into a host cell results in the production of monomer units comprising a targeting unit (exemplified by an MHCII-specific scFv), a multimerization unit (exemplified by a hinge/$C_H3$ domain), and different antigenic units (exemplified by HA from four different influenza subtypes). The individual monomer units associate with another monomer unit to form a mixture of multimer (e.g., dimer) molecules. The mixture of multimer molecules comprises multimers with identical antigenic units and multimers molecules with different antigenic units.

It will be recognized that the constructs may also be used to produce polypeptide vaccine compositions by expressing suitable expression vectors comprising the constructs in a host cell. Accordingly, the present invention also provides vaccine compositions comprising a mixture of multimeric protein molecules, wherein the mixture of multimeric protein molecules comprises a mixture of at least three different fusion protein monomers comprising a targeting unit, a multimerization domain, and an antigenic unit in operable association, wherein the antigenic unit for each of the three different fusion protein monomers differ by encoding different variant target antigenic proteins, and wherein the multimeric protein molecules comprise two of said monomers joined by association of the multimerization domains.

In preferred embodiments, the different antigenic units are variants of a target antigenic protein, for example an antigenic protein from a pathogen such as a virus, bacterium, fungus or protozoa, or a target cancer antigen. In some embodiments, the variants of a target antigenic protein are variants of the target antigenic protein from different strains of a target pathogen such as different strains of a virus, bacterium, fungus, or protozoan. In some embodiments, the variants of a target antigenic protein are variants of the target antigenic protein from different species or genera of a target pathogen such as different species or genera of a virus, bacterium, fungus, or protozoan. In some embodiments, the variants may be defined by the degree of identity of sequence shared by the variants of the target antigenic protein. A high degree of sequence identity is not required as variants target antigenic proteins from different strains of, for example, the same pathogenic organism may be quite diverse in sequence. In some embodiments, the variants may have about greater than 30%, 40%, 50%, 60%, 70%, 80%, 90%, 95%, 96%, 97%, 98% or 99% sequence identity. Accordingly, the DNA vaccine and vaccine compositions of the present invention may comprise sequences encoding 2, 3, 4, 5, 6, 7, 8, 9, 10, 11, 12, 13, 14, 15, 16, 17, 18, 19, or 20 variant target antigenic proteins, or from 2 to 10, 2 to 20, 2 to 30, 2 to 50, 3 to 10, 3 to 20, 3 to 30, 3 to 50, 4 to 10, 4 to 20, 4 to 30, 4 to 50, 5 to 10, 5 to 20, 5 to 30, 5 to 50, 6 to 10, 6 to 20, 6 to 30, or 6 to 50 variant target antigenic proteins, or greater than 2, 3, 4, 5, 6, 7, 8, 9 or 10 variant target antigenic proteins.

The constructs, components of the constructs, vaccines and uses of the vaccines are described in more detail below.

Antigenic Units

The vaccine molecules of the present invention preferably comprise different antigenic units that are variants of a target antigenic protein, for example an antigenic protein from a pathogen such as a virus, bacterium, fungus or protozoa, or a target cancer antigen. As described above, the variants may be defined by the degree of identity of sequence shared by the variants of the target antigenic protein. In some embodiments, the variants may have about greater than 30%, 40%, 50%, 60%, 70%, 80%, 90%, 95%, 96%, 97%, 98% or 99% sequence identity. According to the present technology, an antigenic unit comprises an antigen, which is a substance that evokes the production of one or more antibodies in an organism such as a subject. Each antibody binds to a specific antigen. In some contexts, the term refers to any molecule or molecular fragment that can be bound by a major histocompatibility complex (MHC) and presented to a T-cell receptor.

In some contexts, an immunogen is a specific type of antigen. An immunogen is a substance that induces an adaptive immune response if injected alone (or, e.g., as a part of an antigenic unit of a multimeric vaccine molecule). Thus, an immunogen induces an immune response, whereas an antigen combines with the products of an immune response (e.g., antibodies) once they are made. As an aspect of the instant technology, "antigen" is used in its broadest sense to refer to a molecule, substance, chemical, or polymer such as a protein, polypeptide, and/or peptide against which an immune response is induced in a subject, e.g., as a prophylactic measure or as a treatment, whether it can be otherwise characterized as an immunogen and/or an antigen.

At the molecular level, an antigen can sometimes be characterized by its ability to be "bound" at the antigen-binding site of an antibody. Antibodies discriminate between the specific molecular structures present on the surface of the antigen. Antigens are usually proteins (e.g., polypeptides, peptides, proteins) or polysaccharides that are present, e.g., as parts (coats, capsules, cell walls, flagella, fimbrae, and toxins) of bacteria, viruses, and other microorganisms. Lipids and nucleic acids can be made antigenic by combining them with proteins and polysaccharides.

Cells present their immunogenic antigens to the immune system via a histocompatibility molecule. Depending on the antigen presented and the type of the histocompatibility molecule, several types of immune cells can become activated. By endocytosis or phagocytosis, exogenous antigens are taken into the antigen-presenting cells (APCs) and processed into fragments. APCs then present the fragments to T helper cells (CD4+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles.

According to embodiments of the technology, the multimeric vaccine molecule can be extended to a general medical treatment through induction of an immune response against any polypeptide of any origin. It is possible to incorporate any antigenic sequence provided it is of sufficient length to allow proper folding of the polypeptide. This sequence may be derived from, e.g., a pathogen of a cancer protein. In some embodiments, the target antigenic protein is a protein (or nucleic acid encoding a protein) used therapeutically to induce immune responses that will aid or remedy disease progression (e.g., viral infection, autoimmune diseases, or cancer).

In some embodiments, the molecule of interest is a pathogen-derived antigen (e.g., a nucleic acid or a polypeptide encoding an antigen or antigens from a pathogen). Exemplary pathogenic organisms include, but are not limited to, bacteria, viruses, fungi and protozoa. In some preferred embodiments, the pathogen-derived antigen is influenza hemagglutinin (HA). In some particularly preferred embodiments, the HA is from a group 1 influenza virus. In some embodiments, the group 1 influenza viruses are selected from the group consisting of three or more (i.e., 3 or more, 4 or more, five or more or all six) of H5, H6, H8, H9, H11, and H13.

Antigens from other pathogenic organisms may also be used in the fusion of the present invention. Exemplary pathogens from which antigens may be obtained from include, but are not limited to, In some embodiments, the microorganism is *Bacillus*, including *Bacillus anthracis; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *Y. lamblia, Y. pestis, Pseudomonas*, e.g. *P. aeruginosa, P. putida; Chla-* mydia, e.g. *C. trachomatis;* Bordetella, e.g. *B. pertussis; Treponema*, e.g. *T. palladium; B. anthraces, Y. pestis, Brucella* spp., *F. tularensis, B. mallei, B. pseudomallei, B. mallei, B. pseudomallei, C. botulinum, Salmonella* spp., SEB *V. cholerae* toxin B, *E. coli* O157:H7, *Listeria* sp., *Trichosporon beigelii, Rhodotorula* species, *Hansenula anomala, Enterobacter* sp., *Klebsiella* sp., *Listeria* sp., *Mycoplasma* ssp., *Francisella* spp., *Bartonella* spp., *Borrelia* spp., *Campylobacter* spp., *Chlamydia* spp., *Simkania* spp., *Ehrlichia* spp., *Enterococcus* spp., *Coccidioides* spp., *Bordetella* spp., *Coxiella* spp., *Ureaplasma* spp., *Trichomatis* spp., *Helicobacter* spp., *Legionella* spp., *Mycobacterium* spp., *Corynebacterium* spp., *Rhodococcus* spp., *Rickettsia* spp., *Arcanobacterium* spp., *Listeria* spp., *Treponema* spp., *Brucella* spp., *Campylobacter* spp., *Pasteurella* spp., *Pseudomonas* ssp., *Burkholderii* spp. and the like, orthomyxoviruses, (e.g. influenza virus), paramyxoviruses (e.g., respiratory syncytial virus, mumps virus, measles virus), adenoviruses, rhinoviruses (human and porcine), coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B, C and E), herpesviruses (e.g., Herpes simplex virus, HV-I and HV-II, varicella-zoster virus, cytomegalovirus, Epstein-Barr virus), rotaviruses, Norwalk viruses, hantavirus, arenavirus, rhabdovirus (e.g. rabies virus), retroviruses (including HIV-1, HIV-2, HTLV-I and -II), papovaviruses (e.g. papillomavirus), polyomaviruses, picornaviruses, Dengue virus, Filoviruses (e.g., Marburg and Ebola viruses), Hantavirus, Rift Valley virus, HHV-8, Human papillomavirus, Bovine leukemia virus, Influenza virus, Guanarito virus, Lassa virus, Measles virus, Rubella virus, Mumps virus, Chickenpox (Varicella virus), Monkey pox, Epstein Bahr virus, Parvovirus B19, Hantaan virus, Sin Nombre virus, Venezuelan equine encephalitis, Sabia virus, West Nile virus, Yellow Fever virus, and the like, causative agents of transmissible spongiform encephalopathies, Creutzfeldt-Jakob disease agent, variant Creutzfeldt-Jakob disease agent, *Candida* strains including *C. glabrata, C. albicans, C. krusei, C. lusitaniae* and *C. maltosa*, as well as species of *Aspergillus, Cryptococcus, Histoplasma, Coccidioides, Blastomyces*, and *Penicillium, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi, Ancylostama, Strongylus, Trichostrongylus, Haemonchus, Ostertagia, Ascaris, Toxascaris, Uncinaria, Trichuris, Dirofilaria, Toxocara, Necator, Enterobius, Strongyloides* and *Wuchereria; Acanthamoeba* and other amoebae, *Cryptosporidium, Fasciola, Hartmanella, Acanthamoeba, Giardia lamblia, Isospora belli, Leishmania, Naegleria, Plasmodium* spp., *Pneumocystis carinii, Schistosoma* spp., *Toxoplasma gondii*, and *Trypanosoma* spp., among other viruses, bacteria, archaea, protozoa, fungi, and the like).

The fusion molecules described herein can further comprise antigens from mammalian targets, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD4OL, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW- MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta7, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein Ll, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (FLAP), PlGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TALI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R3Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSFS (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1 BB CD137, ILA), TNFRSF21 (DR6), TNFRSF22 (DcTRAIL R2TNFRH2), TNFRST23 (DcTRAIL R1 TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSFS (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc variants of the present invention in order to generate an Fc fusion. Thus for example, an Fc fusion that targets EGFR could be constructed by operably linking an Fc variant to EGF, TGF-b, or any other ligand, discovered or undiscovered, that binds EGFR. Accordingly, an Fc variant of the present invention could be operably linked to EGFR in order to generate an Fc fusion that binds EGF, TGF-b, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc variants of the present invention to develop an Fc fusion.

The choice of suitable antigen depends on the desired application. In some embodiments, constructs described herein target pathogen antigens. For anti-cancer treatment it is desirable to have a target whose expression is restricted to the cancerous cells. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. In some cases, antibodies directed against infectious disease agents are used.

In one embodiment, the fusion proteins of the present invention are used for the treatment of autoimmune, inflammatory, or transplant indications. Target antigens and clinical products and candidates that are relevant for such diseases include but are not limited to anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFa, TNFa, TNF-alpha) antibodies such as CDP571, CDP870, D2E7, Infliximab, MAK-195F, and anti-VLA-4 antibodies such as Antegren.

Targeting Units

A method to increase the immunogenicity of protein antigens is to incorporate the antigen into antibodies or antibody fragments that target immune system cells, for example, antigen-presenting cells (APC). APCs process antigens and present them to T-cells for the production of antibodies against the antigens. As such, delivering antigen to APCs provides an efficient route to inducing an immune response to the antigen.

An antigen-presenting cell (APC) is a cell that displays antigen complexes with major histocompatibility complex (MHC) on their surfaces. An APC takes up an antigen, performs antigen processing, and returns all or a portion of the antigen (e.g., an epitope) to the APC's surface within an MHC class II molecule for antigen presentation. The CD4 receptors borne by naive helper T cells ligate MHC class II. The epitope (within the MHC class II molecule) imprints the T cell receptor (TCR) of the naive helper T cell, memorizing that epitope.

T cells cannot recognize, and therefore cannot react to, an isolated antigen. T cells can only react to an antigen that has been processed and presented by cells via an MHC molecule. Most cells in the body can present antigen to CD8+ T cells via MHC class I molecules and, thus, are APCs; in some contexts, the term APC refers to those specialized cells that can prime T cells (e.g., activate a T cell that has not been exposed to antigen, termed a "naïve" T cell). These cells, in general, express MHC class II as well as MHC class I molecules, and can stimulate CD4+ ("helper") cells as well as CD8+ ("cytotoxic") T cells, respectively.

APCs are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the APC. An additional co-stimulatory signal is then produced by the APC, leading to activation of the T cell. APCs include dendritic cells, which have the broadest range of antigen presentation. Activated DCs are especially potent Th cell activators because, as part of their composition, they express co-stimulatory molecules such as B7. In addition, APCs include macrophages, B-cells, and some activated epithelial cells. Cells that can act as APCs when stimulated by certain cytokines (e.g., IFN-γ) include fibroblasts, thymic epithelial cells, thyroid epithelial cells, glial cells (brain), pancreatic beta cells, and vascular endothelial cells.

For example, in some embodiments, the targeting unit comprises a single chain fragment variable targeting unit specific for MHC Class II molecules. A single-chain variable fragment (scFv) is a fusion protein of the variable regions of the heavy and light chains of an immunoglobulin connected with a short linker peptide (e.g., about 10 to about 25 amino acids). The linker is usually rich in glycine for flexibility, as well as serine or threonine for solubility, and can either connect the N-terminus of the heavy chain with the C-terminus of the light chain or vice versa. scFv can be created directly from subcloned heavy and light chains derived from a hybridoma, e.g., from a mammalian cell culture, or in a bacterial cell culture such as a culture of *E. coli*.

The scFvs with a targeting function are either derived from B cell hybridomas expressing monoclonal antibodies (mAbs) that bind to surface molecules on APC, or they may be derived from any source, e.g. phage display libraries. The use of scFvs from B cell hybridomas as the targeting moiety opens for a great range of possible targets due to the large collection of B cell hybridomas that produce mAbs which bind different surface molecules on APC. Furthermore, one may choose the nature of the signal given to the targeted cell by employing agonistic or antagonistic mAbs. Growing knowledge of Ab-Ag interactions will allow the improvement of the binding affinity of such mAbs to their Ag by amino acid replacements in the binding sites. This can be performed by ordinary site-directed mutagenesis. For vaccine purposes, an attractive approach is to target the multimeric vaccine molecule to surface molecules expressed exclusively on subsets of dendritic cells (DC) that are able to initiate a strong, specific immune response towards the patients own Id. Examples of such target surface molecules on APC are MHCII molecules, CD40, CD14, HLA-DP, Toll-like receptors, and chemokine receptors. Accordingly, in some embodiments the scFv is anti-MHC-II or anti-HLA (e.g., HLA-DP), anti-CD14, anti-CD40, or anti-toll-like receptor (anti-toll-like receptor 2). In some embodiments, the targeting unit is a ligand (e.g., soluble CD40 ligand or a chemokine (e.g., RANTES or MIP-1α)), a bacterial antigen (e.g., a flaggelin), Because the targeting scFv is inserted into the V cassette of the expression vector pLNOH2 (Norderhaug, Olafsen et al. 1997), it is easily exchanged with other scFvs Also, antigen may be targeted to antigen presenting cells (APC) by conjugating the antigen to antibodies or other antibody fragments directed against surface molecules (e.g., receptors) on various types of APC. Other targeting units include anti-immunoglobulins (e.g., anti-IgG, anti-IgA, anti-IgM, IgD, etc.), and Fab or Fab' fragments.

Multimerization Units

The multimeric vaccine molecules of the technology comprise a multimerization domain (e.g., a dimerization domain). In particular, each polypeptide of the multimeric vaccine molecule comprises a multimerization unit that interacts specifically with a multimerization domain on the other polypeptide to form the multimerization domain.

In some embodiments, the multimerization domain comprises a hinge region and immunoglobulin domain, e.g., a Ch3 domain, or a sequence that is substantially homologous to the C domain. The multimerization domains are referred to herein as a hinge/$C_H3$ multimerization domain. Suitable hinge/$C_H3$ multimerization domains and reference sequences are described in WO 2004/076489, US20130171140 and US20140234316, each of which is incorporated by reference herein its entirety. In other embodiments, vaccine molecules are constructed by a number of different strategies. Some publications describe the use the $C_H2$ and $C_H3$ domains of IgG for dimerization of selected antigens (e.g., Soleimanpour et al, 2015, Appl Microbiol Biotechnol). In some embodiments, Fab-fragments are used for multimerization (e.g., Mayer et al, 2015, Int J Mol Sci), and some use coupling of antigen to full length antibodies that have been equipped with new V-regions (e.g., Caminschi et al, 2008, Blood; Bonifaz et al, 2002, J Exp Med).

In some embodiments, the multimerization domain comprises a bacterial barnase module and a bacterial barstar module. In some embodiments, the multimerization domain further comprises parts of the hinge region of human IgG3. The *Bacillus amyloliquefaciens* proteins barnase and barstar bind each other with a very high affinity ($K_D$ of ~10-14 M), comparable to that between biotin and streptavidin. The barnase-barstar module can accommodate fusions with scFv N-terminally of barnase and barstar as well as scFv [29] or a second barnase C-terminal of barnase. During the development of embodiments of the present technology, data were collected that extend this finding since scFv specific for either mouse MHC class II (I-$E^d$) or NIP could be expressed N-terminally of barnase and barstar (see Examples).

The technology, however, is not limited to multimeric vaccine molecules comprising CH3 or barnase and barstar. Any multimerization domain can be used, e.g., that comprises two or more multimerization domains that are specific for one another. In some embodiments, a "knobs and holes" system is used (see Xie, et al. 2005 "A new format of bispecific antibody: highly efficient dimerization, expression and tumor cell lysis." J Immunol Methods 296: 95). This system is based on the CH3 domains of human IgG1 Fc fragment to produce the complementary knobs and holes that provide the multimerization domain of the multimeric vaccine molecule. One polypeptide comprises a knobs module and the other polypeptide comprises a holes module.

In still other embodiments, the multimerization domain allows formation of higher order multimers including tetramers, pentamers, hexamers, etc. Suitable multimerization systems are described, for example, in WO2001049866, US2003013844, US20100168390, and U.S. Pat. No. 7,482, 430, each of which is incorporated herein by reference in its entirety, and also in Meier et al., J Mol Biol. (2004) 344(4):1051-69 and Kabanova et al., PNAS (2014) 111(5): 17965-17970, each of which is incorporated by reference herein in its entirety.

DNA Vaccines

The technology provided herein provides DNA vaccines comprising nucleic acids encoding multimeric vaccine molecule. In some embodiments, a single nucleic acid comprises the two polypeptides that multimerize to form the multimer. In some embodiments, two or more separate nucleic acids comprise the two polypeptides that multimerize to form the multimer (e.g., one nucleic acid encodes one polypeptide and the other nucleic acid encodes the other nucleic acid). In various embodiments, the nucleic acids are any nucleic acid that can be introduced into a cell and from which a polypeptide can be expressed in vivo.

In these embodiments, the DNA vaccine comprises DNA molecules encoding the fusion constructs described above (i.e., a targeting unit operably linked to an antigenic unit via a multimerization domain and/or other linkers), alone or in association with other desired sequences. DNA vaccines, like peptide-based vaccines, are advantageous in being relatively easy and inexpensive to manufacture, and are not individualized for patients, as are dendritic cell-based vaccines. Unlike recombinant protein vaccines, in which the antigen is taken up by antigen presenting cells and expressed predominantly in the context of MHC class II, DNA in nucleic acid vaccines is taken up and expressed by antigen-presenting cells directly, leading to antigen presentation through both naturally processed MHC class I and II epitopes.

In some embodiments, DNA vaccines comprise nucleic acids encoding a fusion construct described herein in a vector suitable for expression of the nucleic acid. In some embodiments, the nucleic acid is expressed in an expression cassette. In particular embodiments, the expression cassette is a eukaryotic expression cassette. The term "eukaryotic expression cassette" refers to an expression cassette which allows for expression of the open reading frame in a eukaryotic cell. A eukaryotic expression cassette comprises regulatory sequences that are able to control the expression of an open reading frame in a eukaryotic cell, preferably a promoter and polyadenylation signal. Promoters and polyadenylation signals included in the recombinant DNA molecules are selected to be functional within the cells of the subject to be immunized. Examples of suitable promoters, especially for the production of a DNA vaccine for humans, include but are not limited to promoters from cytomegalovirus (CMV), such as the strong CMV immediate early promoter, Simian virus 40 (SV40), Mouse Mammary Tumor Virus (MMTV), Human Immunodeficiency Virus (HIV), such as the HIF Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals.

Other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

The present invention is not limited by the particular formulation of a vaccine composition. When the vaccine is a DNA vaccine, the vaccine may preferably be provided in saline or other physiologically acceptable solution or buffer. In some embodiments, the DNA is administered intramuscularly by needle injection into one or tissues. In some embodiments, an effective route is intramuscular injection into the hind leg quadriceps or tibialis anterior, followed by intradermal injection. These routes usually provoke strong, antigen-specific Th1-biased, humoral and cellular immune responses. In other embodiments, a gene gun is utilized. In these embodiments, the DNA vaccine described is above is coated onto particles, preferably gold particles.

The delivery method generally determines the dose required to raise an effective immune response. Saline injections require variable amounts of DNA, from 10 µg-1 mg, whereas gene gun deliveries require 100 to 1000 times. Generally, 0.2 µg-20 µg are required, although quantities as low as 16 ng have been reported. These quantities vary by species. Mice for example, require approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage".

Vaccines

Multimeric vaccine molecules as provided by the technology provided herein find use in compositions that are vaccines, vaccine components, and/or a pharmaceutical comprising a multimeric vaccine molecule (e.g., a multimeric polypeptide molecule), DNA/RNA sequences, or expression vectors according to the technology. Where appropriate, this pharmaceutical additionally comprises a pharmaceutically compatible carrier. Suitable carriers and the formulation of such pharmaceuticals are known to a person skilled in the art. Suitable carriers are, e.g., phosphate-buffered common salt solutions, water, emulsions, e.g. oil/water emulsions, wetting agents, sterile solutions, etc. The pharmaceuticals may be administered orally or parenterally. The methods of parenteral administration comprise the topical, intra-arterial, intramuscular, subcutaneous, intramedullary, intrathekal, intraventricular, intravenous, intraperitoneal, or intranasal administration. The suitable dose is determined by the attending physician and depends on different factors, e.g. the patient's age, sex and weight, the kind of administration etc.

In one aspect, vaccines or vaccine components are used to immunize mice to produce hybridomas. In some embodiments, the vaccine is for an infectious disease; in other embodiments the vaccine is a therapeutic vaccine for a cancer. Infectious diseases for which a vaccine may be constructed include but are not limited to viral diseases (including rotavirus, norovirus, rabies, influenza virus, herpesvirus, etc.), bacterial diseases (e.g., gonorrhea, streptococcal pneumonia, tuberculosis, tularemia, etc), fungal diseases (e.g., histoplasmosis, blastomycosis, and candidiasis) and protozoal diseases (e.g., cryptosporidiosis, leishmaniasis, filariasis, etc). Examples of cancers which may respond to therapeutic vaccination are, e.g., cervical cancer, melanoma, and breast cancer. In some embodiments, the vaccine is for human use and in some embodiments it is for vaccination of animals, e.g., livestock, companion animals, and any other type of animal (fish, wildlife, etc.). Said vaccines can further also be applied in vitro to cells derived from a subject (e.g., a patient) to cause APC binding and presentation; said cells may then be returned to the host (subject, patient) of origin.

In some embodiments, nucleic acids expressing the polypeptides of the multimeric vaccine molecule are present in a host cell in vitro for the production of the multimeric vaccine molecule. Recombinant methods for producing polypeptides in a cell culture are well known in the art. For example, in some embodiments, the polypeptides of the multimeric vaccine molecule are expressed in a bacterial culture such as a culture of E. coli and the polypeptides of the multimeric vaccine molecule are purified and isolated from the culture to provide the vaccine. In some embodiments, the host cell is a eukaryotic cell kept in cell culture (e.g., transfected into NSO cells, 293E cells and Cos-7 cells) and may or may not by a transformed cell in some embodiments.

In one embodiment, the multimeric vaccine molecule is administered parenterally. In another embodiment the multimeric vaccine molecule is administered to a mucosal surface such as the nasal cavity or other mucosa. In another particular embodiment the multimeric vaccine molecule is administered orally so as to permit presentation to the buccal or gastrointestinal mucosa. In some forms of oral administration the multimeric vaccine molecule is encapsulated in an enteric capsule or gel capsule. In yet other embodiments the multimeric vaccine molecule is combined into a chewable form. When the delivery is to an animal the multimeric vaccine molecule can be incorporated into a bait or foodstuff. In some embodiments, the multimeric vaccine molecule can be applied topically to the skin.

In some embodiments, the present invention provides vaccine compositions comprising a multimeric vaccine molecule as provided herein. The present invention is not limited by the particular formulation of a composition comprising a multimeric vaccine molecule. Indeed, a vaccine composition of the present invention may comprise one or more different agents in addition to the multimeric vaccine molecule. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprising a multimeric vaccine molecule comprises an agent or co-factor that enhances the ability of the antigenic unit to induce an immune response (e.g., an adjuvant). In some preferred embodiments, the presence of one or more co-factors or agents reduces the amount of antigenic unit required for induction of an immune response (e.g., a protective immune response (e.g., protective immunization)). In some embodiments, the presence of one or more co-factors or agents is used to skew the immune response towards a cellular (e.g., T-cell mediated) or humoral (e.g., antibody-mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995, incorporated by reference herein in its entirety for all purposes. The present invention is not limited by the type of adjuvant utilized (e.g., for use in a composition (e.g., a pharmaceutical composition)). For example, in some embodiments, suitable adjuvants include an aluminium salt such as aluminium hydroxide gel (e.g., alum) or aluminium phosphate. In some embodiments, an adjuvant may be a salt of calcium, iron, or zinc, or it may be an insoluble suspension of acylated tyrosine, or acylated sugars, cationically or anionically derivatized polysaccharides, or polyphosphazenes.

In general, an immune response is generated to an antigen through the interaction of the antigen with the cells of the immune system. Immune responses may be broadly categorized into two categories: humoral and cell-mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an antigenic unit). Immune responses can be measured in many ways including activation, proliferation, or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1-type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF, and low levels of TNF-α. Th1 type cytokines promote both cell-mediated immunity and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising an antigenic unit (e.g., multimeric vaccine molecule as provided by the technology described). However, in other embodiments, the present invention provides a method of stimulating a Th2-type immune response in a subject (e.g., if balancing of a T cell mediated response is desired) comprising administering to a subject a composition comprising an antigenic unit (e.g., a multimeric vaccine molecule as provided by the technology described). In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular, 3-de-O-acylated monophosphoryl lipid A (3D-MPL)), is used. 3D-MPL is a well known adjuvant manufactured by Ribi Immunochem, Montana. It is often supplied as a mixture of 3-de-O-acylated monophosphoryl lipid A with either 4, 5, or 6 acylated chains. In some embodiments, diphosphoryl lipid A and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 micrometers in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree Quillaja Saponaria Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146,431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety).

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activates various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63), LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., WO93/13202 and WO92/19265, each of which is hereby incorporated by reference), and other immunogenic substances (e.g., that enhance the effectiveness of a composition of the present invention) are used with a composition comprising a multimeric vaccine molecule of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising a multimeric vaccine molecule, or the adjuvant may be formulated with carriers, for example liposomes or metallic salts (e.g., aluminium salts (e.g., aluminium hydroxide)) prior to combining with or co-administration with a composition.

In some embodiments, a composition comprising a multimeric vaccine molecule comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a multimeric vaccine molecule comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives is contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a multimeric vaccine molecule) enhances induction of an immune response in a subject (e.g., administered a composition of the present invention) due to an increase in duration and/or amount of exposure to an antigenic unit that a subject experiences when a mucoadhesive is used compared to the duration and/or amount of exposure to a multimeric vaccine molecule in the absence of using the mucoadhesive.

In some embodiments, a composition of the present invention may comprise sterile aqueous preparations. Acceptable vehicles and solvents include, but are not limited to, water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a multimeric vaccine molecule of the present invention can be used therapeutically (e.g., to enhance an immune response) or as a prophylactic (e.g., for immunization (e.g., to prevent signs or symptoms of disease)). A composition comprising a multimeric vaccine molecule of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal, and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the route of administration as it has been shown that mucosal administration of antigens induces protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). In addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a multimeric vaccine molecule of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In some embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this invention. Compositions of the present invention may also be administered via the oral route. Under these circumstances, a composition comprising a multimeric vaccine molecule may comprise a pharmaceutically acceptable excipient and/or include alkaline buffers or enteric capsules. Formulations for nasal delivery may include those with dextran or cyclodextran and saponin as an adjuvant.

Compositions of the present invention may also be administered via a vaginal route. In such cases, a composition comprising a multimeric vaccine molecule may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising a multimeric vaccine molecule is administered to a mucosal surface of a subject in either a priming or boosting vaccination regime. Alternatively, in some embodiments, the composition is administered systemically in either a priming or boosting vaccination regime. In some embodiments, a composition comprising a multimeric vaccine molecule is administered to a subject in a priming vaccination regimen via mucosal administration and a boosting regimen via systemic administration. In some embodiments, a composition comprising a multimeric vaccine molecule is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal, or intravenous administration. A composition comprising a multimeric vaccine molecule may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention is a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers, and/or other agents useful in therapy. Also, the use of liposomes, microcapsules or microspheres, inclusion complexes, or other types of carriers is contemplated.

Thus, in some embodiments, a composition comprising a multimeric vaccine molecule of the present invention may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance a immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., E. coli). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, transdermal, intranasal, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies, and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics, or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the antigenic unit or other components of the formulation. In some embodiments, immunostimulatory compositions of the present invention are administered in the form of a pharmaceutically acceptable salt. When used, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, vaccine compositions are co-administered with one or more antibiotics. For example, one or more antibiotics may be administered with, before and/or after administration of the composition. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

Numerous antimicrobial agents are currently available for use in treating bacterial, fungal, and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a vaccine composition comprising a multimeric vaccine molecule with one or more additional active and/or immunostimulatory agents (e.g., a composition comprising a different antigenic unit, an antibiotic, antioxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a multimeric vaccine molecule is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an antigenic unit or organism from which the antigenic unit is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of the composition) may have a stronger immune response to an antigenic unit than a subject administered a composition via just one route.

Other delivery systems can include time-release, delayed release, or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a vaccine composition of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of a nanomulsion and antigenic unit present in the concentrated composition.

Concentrated compositions are contemplated to be useful in a setting in which large numbers of subjects may be administered a composition of the present invention (e.g., an immunization clinic, hospital, school, etc.). In some embodiments, a composition comprising a multimeric vaccine molecule of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an antigenic unit in a boost dose enables vigorous systemic immunity in a subject. The boost can be with the same formulation given for the primary immune response, or can be with a different formulation that contains the antigenic unit. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing albumin variant, antigenic units, and other components and for screening for new components. Thus, it is not intended that the present invention be limited to any particular subject and/or application setting.

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

EXAMPLES

Example 1

Materials and Methods
Construction of APC-Targeted DNA Vaccines

Vaccine plasmids were constructed as previously described (14, 16). Briefly, HA from A/Hong Kong/483/97 (H5N1), A/northern shoveler/California/HKWF115/07 (H6N1), A/pintail duck/Alberta/114/1979 (H8N4), A/Hong Kong/1073/99 (H9N2), A/duck/Yangzhou/906/2002 (H11N2), and A/black-headed gull/Netherlands/1/00 (H13N8) were picked up by PCR from cDNA (VG11689-C; VG11723-C; VG11722-C; VG11229-C; VG11705-C, VG11721-C, all from Sino Biological Inc., Beijing, China), and cloned into SfiI-sites in the CMV-based pLNOH2 vector (27). Primers used were: $H5_{17}5'$: ggc ctc ggt ggc ctg gac cag att tg (SEQ ID NO:1), $H5_{532}3'$: acc ggc cct gca ggc ctc act ggt agg tgc cca tac tct c (SEQ ID NO:2), $H6_{23}5'$: ggc ctc ggt ggc ctg gac aag aft tg (SEQ ID NO:3), $H6_{547}3'$: acc ggc cct gca ggc ctc aca ggg agg ag (SEQ ID NO:4), $H8_{24}5'$: ggc ctc ggt ggc ctg gac agg att tg (SEQ ID NO:5), $H8_{547}3'$: acc ggc cct gca ggc ctc aca ggg agg c (SEQ ID NO:6), $H11_{23}5'$: ggc ctc ggt ggc ctg gat gag att tg (SEQ ID NO:7), $H11_{546}3'$: acc ggc cct gca ggc ctc aca ggg agg ag (SEQ ID NO:8), $H13_{25}5'$: ggc ctc ggt ggc ctg gac agg att tg (SEQ ID NO:9), $H13_{546}3'$: acc ggc cct gca ggc ctc aaa tgc tgg ag (SEQ ID NO:10). The cDNA of HA from H9 (VG11229-C) was delivered without aa 530-541. In order to insert the remaining C-terminal amino acids, and as such generate a gene that would resemble the other HAs with respect to inclusion of the transmembrane region, the following primers were used to insert an extension to the 3' end: $H9_{19}5'$: ggc ctc ggt ggc ctg gac aag att tg (SEQ ID NO:11) and $H9_{529}3'$: cag gga gga cac tgt gct gta gat ggt cag aat ctt gta gg tg (SEQ ID NO:12), followed by $H9_{19}5'$ and $H9_{541}3'$: acc ggc cct gca ggc ctc aca ggg agg ac (SEQ ID NO:13).

SEQ ID NO:14 provides the amino acid sequence for MHC-II-targeted HA from H1N1 influenza. The other HAs used (See FIG. 7) were inserted identically.

(SEQ ID NO: 14)
VQLTQSPASLAVSLGQRATISCRASKSVSTSGYSYMHWYQQKPGQPPKLLIYLTSNLES

GVPARFSGSGSGTDFTLNIHPVEEEDAATYYCQHSRELPWTFGGGTKLEIKGGGGSGGG

GSGGGGSQVQLQQSGPDLVKPGASVTISCKASGYAFSSSWMSWLKQRPGKGLEWIGWI

FPRDGDTNYNGKFKGKATLTADKSSSTAYMQLSSLTSEDSAVYFCARRGDYHYGMDY

WGQGTSVTVSSELKTPLGDTTHTEPKSCDTPPPCPRCPGGGSSGGGSGGQPREPQVYTL

```
PPSREEMTKNQVSLTCLVKGFYPSDIAVEWESSGQPENNYNTTPPMLDSDGSFFLYSKL

TVDKSRWQQGNIFSCSVMHEALHNRFTQKSLSLSPGKGLGGLRDTLCIGYHANNSTDT
VDTVLEKNVTVTHSVNLLEDKHNGKLCKLRGVAPLHLGKCNIAGWILGNPECESLSTA

SSWSYIVETSSSDNGTCYPGDFIDYEELREQLSSVSSFERFEIFPKTSSWPNHDSNKGVTA

ACPHAGAKSFYKNLIWLVKKGNSYPKLSKSYINDKGKEVLVLWGIHHPSTSADQQSLY

QNADAYVFVGSSRYSKKFKPEIAIRPKVRDQEGRMNYYWTLVEPGDKITFEATGNLVV

PRYAFAMERNAGSGIIISDTPVHDCNTTCQTPKGAINTSLPFQNIHPITIGKCPKYVKSTK

LRLATGLRNVPSIQSRGLFGAIAGFIEGGWTGMVDGWYGYHHQNEQGSGYAADLKST

QNAIDEITNKVNSVIEKMNTQFTAVGKEFNHLEKRIENLNKKVDDGFLDIWTYNAELLV

LLENERTLDYHDSNVKNLYEKVRSQLKNNAKEIGNGCFEFYHKCDNTCMESVKNGTY

DYPKYSEEAKLNREEIDGVKLESTRIYQILAIYSTVASSL
```

Amino acids 1-110: αMHC-II VL, (VQLT, etc.)

Amino acids 111-125: Linker, (GGGG, etc.)

Amino acids 126-245: αMHC-II VH, (QVQL, etc.)

Amino acids 246-272: Hinge, H1 + H4, (ELKT etc.)

Amino acids 273-394: CH3 (GGGS etc.)

Amino acid 395: R to make the construct more hydrophilic (R)

Amino acids 396-919: HA from influenza A/California/4/2009 (H1N1) ( DTLC, etc.)

ELISA of Vaccine Proteins

Vaccine plasmids were transiently transfected into HEK 293E cells by addition of 1 μg DNA and Lipofectamine (11668-019, Invitrogen, Life Technologies, CA, US), and supernatants assayed in ELISA as previously described (16). Briefly, 96 well-plates (Costar 3590, Sigma-Aldrich, MO, US) were coated with either anti human IgG ($C_H3$ domain) (1 μg/ml) (MCA878G, AbD Serotec, CA, US) or NIP-BSA (1:1000), and vaccine proteins in transfected supernatants detected with biotinylated anti human IgG ($C_H3$ domain) (HP6017, B3773-.2ML, Sigma, MO, US) (1:3000) and alkaline phosphatase conjugated Streptavidin (RPN1234V, GE Healthcare, Buckinghamshire, UK) (1:3000). The plates were developed using Phosfatase Substrate (P4744-10G, Sigma Aldrich, MO, US), and read with a Tecan reader (Tecan, Switzerland) using the Magellan version 5.03 program.

Animals

Six to twelve weeks-old BALB/cAnN mice were used (Taconic, Denmark). The animals were housed under minimal disease conditions at Oslo University Hospital, Oslo, Norway. Experiments were approved by the Norwegian Animal Research Authority (NARA), Norway.

Viruses

Influenza A/Puerto Rico/8/1934 (H1N1) and A/California/7/2009 (H1N1) were kindly provided by Anna Germundsson Hauge at the National Veterinary Institute, Oslo, Norway. The viruses were propagated by inoculating virus into the allantoic cavity of 10-day-old embryonated chicken eggs. Allantoic fluid was harvested and confirmed negative for bacterial contaminations. $TCID_{50}$ was determined.

Serum ELISA

ELISA 96-well plates (Costar 3590) were coated with one of the following recombinant influenza HA proteins: A/Puerto Rico/8/1934 (H1N1) (11684-VO8H, Sino Biological), A/Hong Kong/483/97 (H5N1) (11689-VO8H, Sino Biological), A/northern shoveler/California/HKWF115/07 (H6N1) (MBS434125 MyBioSource, CA, US, or 11723-V08H, Sino Biological), A/pintail duck/Alberta/114/1979 (H8N4) (11722-V08H, Sino Biological), A/Hong Kong/1073/99 (H9N2) (11229-V08H, Sino Biological), A/duck/Yangzhou/906/2002 (H11N2) (11705-V08H, Sino Biological), A/black-headed gull/Netherlands/1/00 (H13N8) (11721-V08H, Sino Biological), A/Shanghai/1/2013 (H7N9) (40104-V08B, Sino Biological), or A/Hong Kong/1/1968 (H3N2) (40116-V08B, Sino Biological). Alternatively, plates were coated with inactivated virus: A/Puerto Rico/8/1934 (H1N1) (Charles River, MA, US) (1:1600), or A/California/7/2009 (H1N1) (Pandemrix, GlaxoSmithKline, Brentford, UK) (1:50). The coated plates were blocked, and serial dilutions of mouse sera were added to the ELISA-plates. Next, alkaline phosphatase conjugated anti mouse IgG (100M4816, Sigma) (1:5000) was added, and plates developed as described above.

Microneutralization Assay

BALB/c mice (n=6) were vaccinated thrice with DNA immediately followed by skin electroporation (EP) (week 0, 4, 12). Blood was harvested by saphenous vein puncture, and sera separated by centrifugation. The microneutralization assay was set up as previously described (16). Briefly, equal amounts of serum from individual mice were pooled by group, and incubated with receptor destroying enzyme (Denka Seiken, Tokyo, Japan). The enzyme was then deactivated at 56° C. for 1.5 h, and serial serum dilutions added in duplicates to 96-well plates (Costar 3590). Diluted virus and controls were added, and plates incubated at 37° C. for 1 h prior to addition of 20.000 MDCK cells/well. Plates were then incubated at 37° C. ON. Next, cells were fixed with 80% acetone solution, and left to air dry before washing with a 0.3% tween washing buffer. Biotinylated H16-L10-4R5 (ATCC, VA, US) was added (1:1000), and plates developed with alkaline phosphatase conjugated Streptavidin (RPN1234V, GE Healtcare) and phosphatase substrate (P4744-10G, Sigma). Plates were read with a Tecan reader using the Magellan version 5.03 program.

Serum Transfer

BALB/c mice (n=7/group for αMHCII-MIX and αNIP-MIX; n=6/group for PR8 and NaCl controls) were vaccinated thrice with 25 μg DNA/EP (week 0, 4, 8). Two weeks after the last vaccination, blood was harvested by cardiac puncture under full sedation, and sera collected by centrifugation. A new cohort of naïve BALB/c mice (n=10/group) were inoculated with 200 μl pooled serum intravenously (i.v.). A lethal PR8 challenge was administered intranasally (i.n.) 24 hours later, and weight loss monitored.

T-Cell Depletion

BALB/c mice (n=10/group) were vaccinated thrice with DNA/EP (week 0, 4, 8). Starting day 12 after the last vaccination, and then every other day until completion of the experiment, mice received intraperitoneal (i.p.) injections of 200 μg anti-CD4 (GK1.5, ATCC) and anti-CD8 (TIB105, ATCC) mAbs, or isotype controls (SRF8-B6 and Y13-238). At day 14 after the last vaccination, mice were challenged with PR8 influenza and monitored for weight loss.

After termination, spleens were harvested, stained, and analyzed by FACS for the extent of T cell depletion. Briefly, single cell suspensions of splenocytes were blocked (30% inactivated rat serum and 0.1 μg/ml HB197, ATCC) and stained with FITC-conjugated mAb against CD19 (35-0193-9500, TONBO, CA, US) (dump gate), Pacific Blue conjugated mAb against CD8a (558106, BD Pharmingen, CA, US), and PerCP/Cy5.5 conjugated mAb against CD4 (100434, BioLegend, CA, US). Samples were run on a LSRII flow cytometer (Becton Dickinson, NJ, US), and data analyzed with the FlowJo software (Version 7.6) (FlowJo, OR, US).

Statistical Methods

Statistical calculations were performed using two-way Anova with Bonferronis multiple comparison test (Graph-Pad Prism 7 Inc. software).

Results

Construction and Characterization of MHCII-Targeted DNA Vaccines Encoding HA from Six Different Influenza Viruses HA from six different subtypes of group 1 influenza viruses [A/Hong Kong/483/97 (H5N1), A/northern shoveler/California/HKWF115/07 (H6N1), A/pintail duck/Alberta/114/1979 (H8N4), A/Hong Kong/1073/99 (H9N2), A/duck/Yangzhou/906/2002 (H11N2) and A/black-headed gull/Netherlands/1/00 (H13N8)] were separately inserted as antigenic units into plasmids encoding an MHCII-targeted DNA vaccine format (14, 16). Each plasmid encoded a chain consisting of (i) a targeting unit (scFv) that directs the vaccine towards MHCII molecules, (ii) a dimerization unit derived from the hinge and $C_H3$ exons of human IgG3, and (iii) one of the six HAs as antigenic unit. The dimerization unit induces formation of homodimeric vaccine proteins following transcription and translation (FIG. 1a). The new vaccines are denoted αMHCII-H5, αMHCII-H6, αMHCII-H8, αMHCII-H9, αMHCII-H11 and αMHCII-H13, respectively. In order to assess the potential effect of MHCII-targeting, equivalent non-targeted control vaccines were constructed where the targeting unit was replaced with a scFv specific for the synthetic hapten NIP (14, 16), presumably not expressed in mice. The non-targeted vaccines are denoted αNIP-H5, αNIP-H6, αNIP-H8, αNIP-H9, αNIP-H11 and αNIP-H13, respectively.

In order to generate comparable results with the different vaccine constructs, the inserted HA genes were generally selected the same way with respect to the included sequences (FIG. 1b). The intrinsic signaling peptides and intracellular domains were removed in order to secure efficient and similar secretion of the different vaccine proteins. The transmembrane region was only partially truncated in order to maintain a well conserved MHC class I T cell epitope in BALB/c mice (IYSTVASSL); such partial inclusion of the transmembrane region did not impede secretion of the vaccine fusion protein containing H1 in previous experiments (16). Employing this strategy, H6, H8, H9, H11 and H13 were secreted. The exception was HA from H5 influenza, where the inclusion of the IYSTVASSL sequence severely reduced secretion efficacy after in vitro transfection. Upon removal of the complete transmembrane region of H5 HA, the construct was secreted to similar levels as the other HA vaccines into supernatants of transiently transfected 293E cells (FIG. 1c). Hence, for the H5 vaccines, the shortened sequence devoid of the transmembrane region was used. As positive controls in some of the experiments, the previously published MHCII-targeted vaccines encoding HA from influenza A/Puerto Rico/8/1934 (H1N1) [PR8] or A/California/07/2009 (H1N1) [Cal07], αMHCII-H1(PR8) and αMHCII-H1(Cal07), respectively were included (16).

A Single DNA Vaccination with MHCII-Targeted HA from Either H5, H6, H8, H9, H11 or H13 Influenzas Induced High Levels of Strain-Specific IgG Responses BALB/c mice were immunized once with 25 μg plasmids encoding either αMHCII-H5, or αMHCII-H6, or αMHCII-H8, or αMHCII-H9, or αMHCII-H11, or αMHCII-H13. In addition, a positive control group was vaccinated with an MHCII-targeted vaccine encoding HA from influenza PR8 (H1N1) [αMHCII-H1(PR8)] (16). The vaccine plasmids were delivered intradermally (i. d.) in combination with electroporation (EP) to secure efficient cellular uptake of DNA (11, 28). Following vaccination, sera were monitored for development of antibodies against recombinant HA from H5, H6, H8, H9, H11, H13, as well as H1(PR8) influenzas. Importantly, vaccination with each of the MHCII-targeted vaccines encoding a particular HA induced strong strain-specific antibodies (FIG. 2a). Thus, as an example, vaccination with αMHCII-H6 induced high IgG titers against recombinant HA from influenza H6, but failed to induce antibodies against HA from influenza H5, H8, H9, H11, H13 or H1 (FIG. 2a, top row, middle panel). Similarly, vaccination with each of the MHCII-targeted vaccines induced comparable high levels of strain-specific antibodies, but failed to induce antibodies against other types of influenza. There is a slight deviation for αMHCII-H5, which induced somewhat lower titers against the homologous HA (top row, left panel). This is consistent with the observation by others that H5 has a low immunogenicity compared to other HAs (29).

Four weeks after a single DNA immunization, mice were infected with a lethal dose of influenza PR8 (H1N1) and monitored for weight loss. In correspondence with the lack of cross-reactive antibodies (FIG. 2a), vaccination with either αMHCII-H5, or αMHCII-H6, or αMHCII-H8, or αMHCII-H9, or αMHCII-H11, or αMHCII-H13, did not protect mice against a challenge with H1N1(PR8) influenza virus (FIG. 2b). By contrast, mice immunized with αMHCII-H1(PR8) were completely protected, consistent with previous results (16).

A Mixture of Six Different MHCII-Targeted HAs (αMHCII-MIX) Induced IgG Responses Against Each of the Included HAs Conventional influenza vaccines contain three different strains of influenza. Here, it was examined whether a mixture of MHCII-targeted HA from six different group 1 A strains could induce high levels of antibodies. Thus, equal amounts (4.2 µg DNA) of αMHCII-H5, αMHCII-H6, αMHCII-H8, αMHCII-H9, αMHCII-H11 and αMHCII-H13 were mixed, so that a total of 25 µg DNA was delivered per mouse (αMHCII-MIX). In order to assess the potential enhancement of immune responses resulting from targeting of HA to MHCII molecules, a corresponding mixture of NIP-targeted vaccines (αNIP-MIX, non-targeted control) was prepared.

BALB/c mice were immunized thrice with either αMHCII-MIX or αNIP-MIX (FIG. 3). Antibody responses were detected against recombinant HAs of all subtypes included in the vaccine mixture (H5, H6, H8, H9, H11 and H13). Importantly, a single vaccination was sufficient for induction of detectable antibodies against all HA subtypes (FIG. 3) even though titers were lower than that obtained with immunizations using 25 µg for each DNA vaccine separately (FIG. 2). The first and second boost markedly enhanced antibody levels (FIG. 3) so that they exceeded that seen after a single immunization with 25 µg DNA (FIG. 2). In all instances, responses were increased by immunization with αMHCII-MIX as compared to αNIP-MIX. Moreover, the first and second boost further increased the effect of MHC class II targeting, and statistical significance was reached after the second boost for all HAs except H11, when compared to the non-targeted controls. In conclusion, strong anti-HA IgG antibody responses against HA of each of six very different strains of influenza were induced by their simultaneous delivery in the context of MHCII-targeted DNA vaccines.

Vaccination with αMHCII-MIX Induces Cross-Reactive Antibodies and Protection Against Challenge with Influenza H1N1 (Not Included in the Vaccine Mixture)

It was next tested if the mixture in addition could promote cross-reactive immune responses against subtypes not included in the mixture. To this end, the antibody responses induced after vaccination with αMHCII-MIX or αNIP-MIX against inactivated PR8 and Cal07 in ELISAs were examined (neither of these H1N1 influenzas had been included in the vaccine mixtures). A small but persistent IgG response was detectable against both viruses (FIG. 4a-b). However, the titers after vaccination with αMHCII-MIX were not significantly elevated above that of αNIP-MIX, and sera from neither vaccination could neutralize the H1 viruses in micro-neutralization assays (FIG. 4c-d). The cross-reactive antibodies are likely to be specific for common epitopes in the head region of HA, since an ELISA designed to detect stem-reactive antibodies could not demonstrate significant increases of stem-reactive antibodies after vaccination with αMHCII-MIX or αNIP-MIX (data not shown). As positive controls in these experiments, MHCII-targeted vaccines encoding HA from either PR8 [αMHCII-H1(PR8)] or Cal07 [αMHCII-H1(Cal07)], respectively were included. As previously publications have demonstrated, vaccination with these two constructs elicited strain-specific antibodies with neutralizing activity (16).

Similar to H5, H6, H8, H9, H11 and H13, H1 is a subtype belonging to group 1 influenza viruses. The group is classified based on shared stem structures (30), and it was tested whether vaccination with αMHCII-MIX and αNIP-MIX could induce antibodies against subtypes classified as group 2 members. Thus, sera were examined for reactivity against HA from H3 and H7 subtypes of influenza. No significant H3- or H7-reactive antibody responses were detectable by ELISA when compared to vaccination with NaCl, although sporadic responses were observed in a few mice.

Despite the absence of H1-reactive neutralizing antibodies in sera (FIG. 4c-d), mice were challenged with a lethal dose of Cal07 (FIG. 4e-f) or PR8 (FIG. 4g-h). As positive controls, and consistent with previous results, mice immunized with either αMHCII-H1(PR8) or αMHCII-H1(Cal07) were protected against both of these H1 viruses due to cross-protective T cells (16). More surprisingly, the mice that received the αMHCII-MIX were protected against both weight loss and death after challenge with both Cal07 ($p<0.01$) (FIG. 4e-f) and PR8 ($p=0.01$) (FIG. 4g-h). In the Cal07-challenge, there was also significant less weight loss and better survival in the αMHCII-MIX-group compared to the non-targeted controls. In conclusion, vaccination with αMHCII-MIX confers a cross-reactive immune response that protects mice against heterosubtypical challenge with two different H1-subtypes (Cal07 and PR8).

Cross-Protection After αMHCII-MIX Vaccination is Mediated by Antibodies

To test if antibodies contributed to the observed protection, sera collected two weeks after three vaccinations (week 0, 4, 8) were transferred i.v. to BALB/c mice, followed by challenge with H1 (PR8). Mice receiving sera from animals vaccinated with αMHCII-MIX had a significantly delay in weight loss and death, compared to mice vaccinated with αNIP-MIX or NaCl ($p<0.001$) (FIG. 5a-b). On average, disease and death was delayed by 24 h in the mice that received sera from the αMHCII-MIX vaccinated mice compared to αNIP-MIX or NaCl. Thus, vaccination with αMHCII-MIX induced antibodies that weakly protected against the group 1 virus H1 (PR8), a subgroup of HA not included in the vaccine mixture.

The transfer of pooled sera from vaccinated mice constitutes a substantial dilution of donor-derived antibodies in recipients. Thus, to more directly test the efficiency of antibodies in the vaccinated mice, T cells were depleted in thrice-immunized mice prior to a challenge with PR8 virus. The depletion procedure removed over 99% of all $CD4^+$ and $CD8^+$ T cells in the spleen. The results showed that depletion of T-cells prior to influenza challenge had no effect on protection against PR8 (FIG. 5c-d). These data indicate that αMHCII-MIX induced cross-reactive, protective antibodies, in addition to strong antibody responses against each of the six subtypes of influenza HA included in the vaccine mixture. These experiments do not rule out that cross-protective T cells could also pay a role in mice immunized with the αMHCII-MIX.

The possible emergence of pandemic influenzas calls for novel and effective vaccination strategies. Whereas current production strategies are cumbersome and time-consuming, DNA vaccines do not require viral growth in eggs or cells, and allow for rapid production and global deployment should the need arise. It was previously demonstrated that targeting of HA from H1N1 influenzas to MHCII molecules increases immune responses after DNA vaccination (16), and that APC-targeted DNA vaccines can be produced within one month after identification of the viral sequence (26). Besides enhanced $CD4^+$ and $CD8^+$ T cell responses, increased levels of head-specific neutralizing antibodies were rapidly induced in vaccinated animals (16). Experiments described herein demonstrated that this versatile and flexible format also contributes improved antibody responses when extended to a mixture of six different subtypes of influenza (H5, H6, H8, H9, H11 or H13). Moreover, when the six HA vaccines were mixed and simultaneously injected, antibody responses against the six HAs were maintained.

The levels of antibodies induced against each of the 6 HAs in the DNA vaccine mixture were clearly enhanced if the proteins were targeted to MHCII molecules. It was contemplated that this may be due to the formation of APC-B cell synapses where MHCII-targeted vaccine proteins bridge the two cell types (14, 25, 26). Indeed, APC-B cell synapses have been demonstrated in vitro (31), however, in vivo evidence is lacking. In such an APC-B cell synapse, HA could bind the B cell receptor (BCR) of HA-specific B cells, whereas the MHCII-specific scFv could bind an MHC+ APC. Of note, MHC class II molecules have hitherto been the most efficient target yet observed for induction of antibodies by targeted DNA vaccines (17). One reason might be that MHC class II molecules are highly expressed on many types of professional APC, thus many APC-B cell synapses may form to enhance immune responses.

Putative APC-B cell synapses are, after αMHCII-MIX immunization, likely to contain many different MHCII-targeted HAs. Further, only a single B cell is anticipated to participate in any APC-B cell synapse. Therefore, the inclusion of many different HAs in the vaccine mixture could possibly inhibit B cell responses since only a fraction of HAs displayed in a single synapse will have the ability to bind the BCR of the B cell in the synapse. Thus, the higher number of different HAs that are included in the vaccine mixture, the less efficient crosslinking of a homogenous BCR in the synapse would be expected. If so, there could be a threshold as to the number of different HAs that may be included in the mix before B cell responses are reduced. However, if any single APC can generate not only one but several synapses with distinct B cells, the various HAs could be enriched in the different synapses, each synapse involving distinct B cells of different specificities. If so, the problem of HA dilution in a synapse, with increased number of HAs, would be lessened. Taken together, the data described herein demonstrated that high antibody levels were maintained with a mixture of 6 different MHCII-targeted HAs, a threshold for how many HAs that can be included before compromising induction of strain-specific antibodies is likely to exist.

Previous experiments demonstrated that the MHCII-targeted vaccine proteins are secreted as dimers, and that the two monomeric HAs in the antigenic units of a single dimeric vaccine molecule appear to not interact with each other (16). It is contemplated that the hinge/$CH_3$-dependent dimerization occurs in the endoplasmic reticulum (ER), similar to the assembly of Ig heavy chains. Further, when vaccinating with a mixture, single cells are likely be transfected with most if not all the different plasmids (FIG. 6a). If so, in the ER of each cell, the different vaccine polypeptides are likely to randomly associate into dimeric vaccine proteins expressing either two identical or two different HAs. The number of possible different combinations from n chains expressing n different HAs can be calculated by the formula $[n(n+1)]/2$ (FIG. 6b). Thus, cells transfected with 6 different vaccine plasmids, as used herein, should yield 21 different vaccine dimers, out of which 17% of the possible combinations will express two identical HA monomers of H5, H6, H8, H9, H11 or H13, respectively. It is contemplated that the bivalent vaccine proteins may be more potent than the heterodimeric (univalent) vaccine proteins because the bivalent form may have an increased ability to cross-link BCR of HA-specific B cells. If true, increasing the number of plasmids in the mix while keeping the total DNA amount constant reduces the production of each of the bivalent homodimeric proteins (FIG. 6b), thereby probably reducing their immunogenicity. This effect may be detrimental to the induction of strain-specific antibodies that can confer neutralizing activity against each HA in the vaccine mixture. On the other hand, increasing the number of plasmids may increase the likelihood of eliciting antibody responses to shared subdominant epitopes, such as the HA stem, thus favoring induction of broadly cross-reactive antibodies at the expense of strain-specific antibodies against HA.

In addition to the development of antibody responses specific for each included HA, vaccination with αMHCII-MIX conferred some antibody-mediated protection against influenza subtypes that were not included in the vaccine mixture (H1N1 PR8 and Cal07). Antibodies were of relatively low titers, and reactivity with the stem of HA from H1 and H7 influenzas appeared to differ between individual mice. The cross-reactive antibodies were not neutralizing in in vitro microneutralization assays. However, antibodies could possibly confer protection by complement dependent lysis (CDL) (32), or by antibody dependent cell-mediated cytotoxicity (ADCC) (33-36).

In addition to antibodies, T cells could have contributed to the observed protection. Indeed, cytotoxic T-cells play an important role in the clearance of influenza infected cells (37, 38), and apart from H5 HA, the different HAs included in the vaccine mix share at least one known $H-2K^d$-restricted CD8+ T-cell epitope that could have induced cross-reactive cytotoxic T-cell responses against influenza PR8 (39). In addition to CD8+ T cells, influenza-specific CD4+ T-cells have been shown to correlate with protection against disease (40). Relevant to this, a partially conserved BALB/c CD4+ T-cell epitope is found among the various HAs in the vaccine mix and PR8 (41) (FIG. 1b). Most likely, both antibodies and T cells may have acted in concert to mediate the observed cross-protection against influenza PR8 that was observed in mice vaccinated with the αMHCII-MIX.

Whereas conventional influenza vaccines typically contain two different influenza A subtypes, and one influenza B strain, in experiments described herein, mice were simultaneously injected with MHCII-targeted HAs from six different sub-strains of influenza A. Homologous antibody responses were not impaired by the simultaneous delivery, and strong antibody responses were developed against each vaccine component. This indicates that it would be possible to combine the most relevant seasonal and potential pandemic strains into a single vaccine mixture to confer increased breadth of protection in vaccines. In addition, it was observed that MHCII-targeted vaccination with the HA mixture could raise low levels of cross-reactive antibodies against a subtype that was not included in the vaccine mixture. Thus, the vaccine strategy may also confer some basic protection against an unexpected influenza emergence.

Example 2

This Example describes the effects of epitope dilution on immunization. Mice (F1 of BALB/c and CR9114 gH knock in mice) were immunized on days 0 and 32 as indicated by arrows (FIG. 9), with vaccine mixtures containing hemagglutinin from influenza subtypes H2, H3, H4, H5, H6, H7, H8, H9, H10, H11, H12, H13, H14, H15, H16, H17, and H18, targeted towards either MHC class II molecules, chemokine receptors 1/3/5 with MIP1a, or against the hapten NIP (non-targeted control). Antibody responses were monitored longitudinally by ELISA against recombinant HA proteins from influenza H1 [A/PR/8/1934 (H1N1)], H5 [A/Hong Kong/483/97 (H5N1)], H3 [A/Hong Kong/1/1968 (H3N2)], or H7 [A/Shanghai/1/2013 (H7N9)]. Results (FIG. 9) demonstrated strong antibody induction against vaccine subtypes included in the vaccine mixture (e.g. H5, H3, H7), but also a marked presence of antibodies against a subtype not included in the vaccine mixture (H1).

Mice (F1 of BALB/c and CR9114 gH knock in mice) were immunized on days 0 and 32 as indicated by arrows (FIG. 10), with vaccine mixtures containing hemagglutinin from influenza subtypes H2, H3, H4, H5, H6, H7, H8, H9, H10, H11, H12, H13, H14, H15, H16, H17, and H18, targeted towards either MHC class II molecules, chemokine receptors 1/3/5 with MIP1a, or against the hapten NIP (non-targeted control). At day 55 after the first vaccination, mice were challenged with a lethal dose of influenza A/PR/8/1934 (H1N1) (2.5LD50), and monitored for weight loss. Results (FIG. 10) demonstrated that the APC-targeted vaccines could confer protection (30% for αMHCII-MIX, and 70% for MIP1a-MIX) against an influenza subtype that was not present in the vaccine mixture (H1).

In summary, this example demonstrates that epitope dilution is effective also when the mixture is expanded to HAs from 17 subtypes of influenza (FIG. 9) and when targeted to different receptors on APC (FIG. 10).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

REFERENCES

The following references cited herein are incorporated by reference in their entireties for all purposes.
1. Chen E, Wang F, Ly H, Zhang Y, Ding H, Liu S, Cai J, Xie L, Xu X, Chai C, Mao H, Sun J, Lin J, Yu Z, Li L, Chen Z, Xia S. 2013. The first avian influenza A (H7N9) viral infection in humans in Zhejiang Province, China: a death report. Front Med 7:333-344.
2. Huang Y, Li X, Zhang H, Chen B, Jiang Y, Yang L, Zhu W, Hu S, Zhou S, Tang Y, Xiang X, Li F, Li W, Gao L. 2015. Human infection with an avian influenza A (H9N2) virus in the middle region of China. J Med Virol doi: 10.1002/jmv.24231.
3. To K K, Tsang A K, Chan J F, Cheng V C, Chen H, Yuen K Y. 2014. Emergence in China of human disease due to avian influenza A(H10N8)—cause for concern? J Infect 68:205-215.
4. Tran T H, Nguyen T L, Nguyen T D, Luong T S, Pham P M, Nguyen v V, Pham T S, Vo C D, Le T Q, Ngo T T, Dao B K, Le P P, Nguyen T T, Hoang T L, Cao V T, Le T G, Nguyen D T, Le H N, Nguyen K T, Le H S, Le V T, Christiane D, Tran T T, Menno de J, Schultsz C, Cheng P, Lim W, Horby P, Farrar J, World Health Organization International Avian Influenza Investigative T. 2004. Avian influenza A (H5N1) in 10 patients in Vietnam. N Engl J Med 350:1179-1188.
5. Wei S H, Yang J R, Wu H S, Chang M C, Lin J S, Lin C Y, Liu Y L, Lo Y C, Yang C H, Chuang J H, Lin M C, Chung W C, Liao C H, Lee M S, Huang W T, Chen P J, Liu M T, Chang F Y. 2013. Human infection with avian influenza A H6N1 virus: an epidemiological analysis. Lancet Respir Med 1:771-778.
6. DiazGranados C A, Denis M, Plotkin S. 2012. Seasonal influenza vaccine efficacy and its determinants in children and non-elderly adults: a systematic review with meta-analyses of controlled trials. Vaccine 31:49-57.
7. Tricco A C, Chit A, Soobiah C, Hallett D, Meier G, Chen M H, Tashkandi M, Bauch C T, Loeb M. 2013. Comparing influenza vaccine efficacy against mismatched and matched strains: a systematic review and meta-analysis. BMC Med 11:153.
8. Partridge J, Kieny M P, World Health Organization HNivTF. 2010. Global production of seasonal and pandemic (H1N1) influenza vaccines in 2009-2010 and comparison with previous estimates and global action plan targets. Vaccine 28:4709-4712.
9. Fineberg H V. 2014. Pandemic preparedness and response—lessons from the H1N1 influenza of 2009. N Engl J Med 370:1335-1342.
10. Perdue M L, Arnold F, Li S, Donabedian A, Cioce V, Warf T, Huebner R. 2011. The future of cell culture-based influenza vaccine production. Expert Rev Vaccines 10:1183-1194.
11. Roos A K, Moreno S, Leder C, Pavlenko M, King A, Pisa P. 2006. Enhancement of cellular immune response to a prostate cancer DNA vaccine by intradermal electroporation. Mol Ther 13:320-327.
12. Broderick K E, Humeau L M. 2015. Electroporation-enhanced delivery of nucleic acid vaccines. Expert Rev Vaccines 14:195-204.
13. Raviprakash K, Porter K R. 2006. Needle-free injection of DNA vaccines: a brief overview and methodology. Methods Mol Med 127:83-89.
14. Fredriksen A B, Sandlie I, Bogen B. 2006. DNA vaccines increase immunogenicity of idiotypic tumor antigen by targeting novel fusion proteins to antigen-presenting cells. Mol Ther 13:776-785.
15. Fredriksen A B, Bogen B. 2007. Chemokine-idiotype fusion DNA vaccines are potentiated by bivalency and xenogeneic sequences. Blood 110:1797-1805.
16. Grodeland G, Mjaaland S, Roux K H, Fredriksen A B, Bogen B. 2013. DNA vaccine that targets hemagglutinin to MHC class II molecules rapidly induces antibody-mediated protection against influenza. J Immunol 191: 3221-3231.
17. Grodeland G, Mjaaland S, Tunheim G, Fredriksen A B, Bogen B. 2013. The specificity of targeted vaccines for APC surface molecules influences the immune response phenotype. PLoS One 8:e80008.
18. Ruffini P A, Grodeland G, Fredriksen A B, Bogen B. 2010. Human chemokine MIP1alpha increases efficiency of targeted DNA fusion vaccines. Vaccine 29:191-199.
19. Grodeland G, Fredriksen A B, Loset G A, Vikse E, Fugger L, Bogen B. 2016. Antigen Targeting to Human HLA Class II Molecules Increases Efficacy of DNA Vaccination. J Immunol 197:3575-3585.

20. Carayanniotis G, Barber B H. 1987. Adjuvant-free IgG responses induced with antigen coupled to antibodies against class II MHC. Nature 327:59-61.
21. Kawamura H, Berzofsky J A. 1986. Enhancement of antigenic potency in vitro and immunogenicity in vivo by coupling the antigen to anti-immunoglobulin. J Immunol 136:58-65.
22. Snider D P, Segal D M. 1987. Targeted antigen presentation using crosslinked antibody heteroaggregates. J Immunol 139:1609-1616.
23. Grodeland G, Fossum E, Bogen B. 2015. Polarizing T and B Cell Responses by APC-Targeted Subunit Vaccines. Front Immunol 6:367.
24. Fossum E, Grodeland G, Terhorst D, Tveita A A, Vikse E, Mjaaland S, Henri S, Malissen B, Bogen B. 2015. Vaccine molecules targeting Xcr1 on cross-presenting DCs induce protective CD8+ T-cell responses against influenza virus. Eur J Immunol 45:624-635.
25. Fredriksen A B, Sandlie I, Bogen B. 2012. Targeted DNA vaccines for enhanced induction of idiotype-specific B and T cells. Front Oncol 2:154.
26. Grodeland G, Bogen B. 2015. Efficient vaccine against pandemic influenza: combining DNA vaccination and targeted delivery to MHC class II molecules. Expert Rev Vaccines 14:805-814.
27. Norderhaug L, Olafsen T, Michaelsen T E, Sandlie I. 1997. Versatile vectors for transient and stable expression of recombinant antibody molecules in mammalian cells. J Immunol Methods 204:77-87.
28. Roos A K, Eriksson F, Timmons J A, Gerhardt J, Nyman U, Gudmundsdotter L, Brave A, Wahren B, Pisa P. 2009. Skin electroporation: effects on transgene expression, DNA persistence and local tissue environment. PLoS One 4:e7226.
29. Treanor J J, Wilkinson B E, Masseoud F, Hu-Primmer J, Battaglia R, O'Brien D, Wolff M, Rabinovich G, Blackwelder W, Katz J M. 2001. Safety and immunogenicity of a recombinant hemagglutinin vaccine for H5 influenza in humans. Vaccine 19:1732-1737.
30. Air G M. 1981. Sequence relationships among the hemagglutinin genes of 12 subtypes of influenza A virus. Proc Natl Acad Sci USA 78:7639-7643.
31. Batista F D, Iber D, Neuberger M S. 2001. B cells acquire antigen from target cells after synapse formation. Nature 411:489-494.
32. Terajima M, Cruz J, Co M D, Lee J H, Kaur K, Wrammert J, Wilson P C, Ennis F A. 2011. Complement-dependent lysis of influenza a virus-infected cells by broadly cross-reactive human monoclonal antibodies. J Virol 85:13463-13467.
33. Hashimoto G, Wright P F, Karzon D T. 1983. Antibody-dependent cell-mediated cytotoxicity against influenza virus-infected cells. J Infect Dis 148:785-794.
34. Greenberg S B, Criswell B S, Six H R, Couch R B. 1978. Lymphocyte cytotoxicity to influenza virus-infected cells: response to vaccination and virus infection. Infect Immun 20:640-645.
35. DiLillo D J, Tan G S, Palese P, Ravetch J V. 2014. Broadly neutralizing hemagglutinin stalk-specific antibodies require FcgammaR interactions for protection against influenza virus in vivo. Nat Med 20:143-151.
36. Jegaskanda S, Job E R, Kramski M, Laurie K, Isitman G, de Rose R, Winnall W R, Stratov I, Brooks A G, Reading P C, Kent S J. 2013. Cross-reactive influenza-specific antibody-dependent cellular cytotoxicity antibodies in the absence of neutralizing antibodies. J Immunol 190:1837-1848.
37. Yap K L, Ada G L, McKenzie I F. 1978. Transfer of specific cytotoxic T lymphocytes protects mice inoculated with influenza virus. Nature 273:238-239.
38. Zweerink H J, Courtneidge S A, Skehel J J, Crumpton M J, Askonas B A. 1977. Cytotoxic T cells kill influenza virus infected cells but do not distinguish between serologically distinct type A viruses. Nature 267:354-356.
39. Tamura M, Kuwano K, Kurane I, Ennis F A. 1998. Definition of amino acid residues on the epitope responsible for recognition by influenza A virus H1-specific, H2-specific, and H1- and H2-cross-reactive murine cytotoxic T-lymphocyte clones. J Virol 72:9404-9406.
40. Wilkinson T M, Li C K, Chui C S, Huang A K, Perkins M, Liebner J C, Lambkin-Williams R, Gilbert A, Oxford J, Nicholas B, Staples K J, Dong T, Douek D C, McMichael A J, Xu X N. 2012. Preexisting influenza-specific CD4+ T cells correlate with disease protection against influenza challenge in humans. Nat Med 18:274-280.
41. Lu I N, Farinelle S, Sausy A, Muller C P. 2016. Identification of a CD4 T-cell epitope in the hemagglutinin stalk domain of pandemic H1N1 influenza virus and its antigen-driven TCR usage signature in BALB/c mice. Cell Mol Immunol doi:10.1038/cmi.2016.20.

We claim:

1. A DNA vaccine comprising three or more different nucleic acid constructs, each of said constructs encoding a fusion protein comprising a targeting unit, a multimerization domain, and an antigenic unit in operable association, wherein said antigenic unit for each of said three or more different nucleic acid constructs differ by encoding different variant target antigenic proteins and wherein when said three or more different nucleic acid constructs are introduced into a cells a random mixture of multimeric protein molecules comprising the same and different variant target antigenic proteins are produced via association of said multimerization domains.

2. The DNA vaccine of claim 1, wherein said multimeric protein molecule is a dimeric protein molecule and multimerization domain is a dimerization domain.

3. The DNA vaccine of claim 2, wherein said multimerization domain is a hinge/$C_H3$ dimerization domain.

4. The DNA vaccine of claim 1, wherein said targeting unit is an antigen binding protein.

5. The DNA vaccine of claim 4, wherein said antigen binding protein is an scFv.

6. The DNA vaccine of claim 1, wherein said targeting unit is an Antigen Presenting Cell (APC) targeting unit.

7. The DNA vaccine of claim 6, wherein said APC targeting unit binds to a target selected from the group consisting of MHC-II molecules, CD40, CD14, HLA-DP, Toll-like receptors, and chemokine receptors.

8. The DNA vaccine of claim 1, wherein said different variant antigenic target proteins have greater than about 30%, 40%, 50%, 60%, 70%, 80%, 90% or 95% sequence identity.

9. The DNA vaccine of claim 1, where said different variant antigenic target proteins are from different strains of an organism.

10. The DNA vaccine of claim 9, wherein said organism is a pathogenic organism.

11. The DNA vaccine of claim 1, wherein said different variant antigenic target proteins are variants of hemagglutinin (HA).

12. The DNA vaccine of claim 11, wherein said vaccine comprises variants of HA from at least three, four, five or six strains of influenza viruses.

13. The DNA vaccine of claim 12, wherein said influenza viruses are group 1 influenza viruses.

14. The DNA vaccine of claim 13, wherein said group 1 influenza viruses are selected from the group consisting of H5, H6, H8, H9, H11, and H13.

15. The DNA vaccine of claim 1, wherein said different variant antigenic target proteins are variants of a cancer antigen.

16. The DNA vaccine of claim 2, wherein said random mixture of dimeric protein molecules comprises a defined number of different dimeric molecules, where said defined number of different dimeric molecules is calculated by the formula $[n(n+1)]/2$ where n is the number of different variant antigenic target proteins.

17. The DNA vaccine of claim 16, wherein the number of different dimeric molecules is 6 when n is 3, 10 when n is 4, 15 when is n 5 and 21 when n is 6.

18. The DNA vaccine of claim 1, wherein the sequence encoding the fusion protein is operably linked to a promoter.

19. A method of immunizing or inducing an immune response to variant target antigenic proteins in a subject comprising administering to said subject a DNA vaccine according to claim 1 to a subject.

* * * * *

SEQUENCE LISTING

<160> NUMBER OF SEQ ID NOS: 22

<210> SEQ ID NO 1
<211> LENGTH: 26
<212> TYPE: DNA
<213> ORGANISM: Artificial sequence
<220> FEATURE:
<223> OTHER INFORMATION: Synthetic

<400> SEQUENCE: 1
ggcctcggtg gcctggacca gatttg          26

<210> SEQ ID NO 2
<211> LENGTH: 40
<212> TYPE: DNA
<213> ORGANISM: Artificial sequence
<220> FEATURE:
<223> OTHER INFORMATION: Synthetic

<400> SEQUENCE: 2
accggccctg caggcctcac tggtaggtgc ccatactctc                               40

<210> SEQ ID NO 3
<211> LENGTH: 26
<212> TYPE: DNA
<213> ORGANISM: Artificial sequence
<220> FEATURE:
<223> OTHER INFORMATION: Synthetic

<400> SEQUENCE: 3
ggcctcggtg gcctggacaa gatttg                                              26

<210> SEQ ID NO 4
<211> LENGTH: 29
<212> TYPE: DNA
<213> ORGANISM: Artificial sequence
<220> FEATURE:
<223> OTHER INFORMATION: Synthetic

<400> SEQUENCE: 4
accggccctg caggcctcac agggaggag                                           29

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
ggcctcggtg gcctggacag gatttg                                              26

<210> SEQ ID NO 6
<211> LENGTH: 28
<212> TYPE: DNA
<213> ORGANISM: Artificial sequence
<220> FEATURE:
<223> OTHER INFORMATION: Synthetic

<400> SEQUENCE: 6
accggccctg caggcctcac agggaggc                                            28

<210> SEQ ID NO 7
<211> LENGTH: 26
<212> TYPE: DNA
<213> ORGANISM: Artificial sequence
<220> FEATURE:
<223> OTHER INFORMATION: Synthetic

<400> SEQUENCE: 7
ggcctcggtg gcctggatga gatttg                                              26

<210> SEQ ID NO 8
<211> LENGTH: 29
<212> TYPE: DNA
<213> ORGANISM: Artificial sequence
<220> FEATURE:
<223> OTHER INFORMATION: Synthetic

<400> SEQUENCE: 8
accggccctg caggcctcac agggaggag                                           29

<210> SEQ ID NO 9
<211> LENGTH: 26

```
<212> TYPE: DNA
<213> ORGANISM: Artificial sequence
<220> FEATURE:
<223> OTHER INFORMATION: Synthetic

<400> SEQUENCE: 9
ggcctcggtg gcctggacag gatttg                                          26

<210> SEQ ID NO 10
<211> LENGTH: 29
<212> TYPE: DNA
<213> ORGANISM: Artificial sequence
<220> FEATURE:
<223> OTHER INFORMATION: Synthetic

<400> SEQUENCE: 10
accggccctg caggcctcaa atgctggag                                       29

<210> SEQ ID NO 11
<211> LENGTH: 26
<212> TYPE: DNA
<213> ORGANISM: Artificial sequence
<220> FEATURE:
<223> OTHER INFORMATION: Synthetic

<400> SEQUENCE: 11
ggcctcggtg gcctggacaa gatttg                                          26

<210> SEQ ID NO 12
<211> LENGTH: 43
<212> TYPE: DNA
<213> ORGANISM: Artificial sequence
<220> FEATURE:
<223> OTHER INFORMATION: Synthetic

<400> SEQUENCE: 12
cagggaggac actgtgctgt agatggtcag aatcttgtag gtg                       43

<210> SEQ ID NO 13
<211> LENGTH: 29
<212> TYPE: DNA
<213> ORGANISM: Artificial sequence
<220> FEATURE:
<223> OTHER INFORMATION: Synthetic

<400> SEQUENCE: 13
accggccctg caggcctcac agggaggac                                       29

<210> SEQ ID NO 14
<211> LENGTH: 918
<212> TYPE: PRT
<213> ORGANISM: Artificial sequence
<220> FEATURE:
<223> OTHER INFORMATION: Synthetic

<400> SEQUENCE: 14
```

Val Gln Leu Thr Gln Ser Pro Ala Ser Leu Ala Val Ser Leu Gly Gln
1               5                   10                  15

Arg Ala Thr Ile Ser Cys Arg Ala Ser Lys Ser Val Ser Thr Ser Gly
            20                  25                  30

Tyr Ser Tyr Met His Trp Tyr Gln Gln Lys Pro Gly Gln Pro Pro Lys
        35                  40                  45

Leu Leu Ile Tyr Leu Thr Ser Asn Leu Glu Ser Gly Val Pro Ala Arg
    50                  55                  60

-continued

```
Phe Ser Gly Ser Gly Ser Gly Thr Asp Phe Thr Leu Asn Ile His Pro
 65                  70                  75                  80

Val Glu Glu Asp Ala Ala Thr Tyr Tyr Cys Gln His Ser Arg Glu
             85                  90                  95

Leu Pro Trp Thr Phe Gly Gly Gly Thr Lys Leu Glu Ile Lys Gly Gly
            100                 105                 110

Gly Gly Ser Gly Gly Gly Gly Ser Gly Gly Gly Ser Gln Val Gln
        115                 120                 125

Leu Gln Gln Ser Gly Pro Asp Leu Val Lys Pro Gly Ala Ser Val Thr
130                 135                 140

Ile Ser Cys Lys Ala Ser Gly Tyr Ala Phe Ser Ser Trp Met Ser
145                 150                 155                 160

Trp Leu Lys Gln Arg Pro Gly Lys Gly Leu Glu Trp Ile Gly Trp Ile
                165                 170                 175

Phe Pro Arg Asp Gly Asp Thr Asn Tyr Asn Gly Lys Phe Lys Gly Lys
            180                 185                 190

Ala Thr Leu Thr Ala Asp Lys Ser Ser Thr Ala Tyr Met Gln Leu
            195                 200                 205

Ser Ser Leu Thr Ser Glu Asp Ser Ala Val Tyr Phe Cys Ala Arg Arg
210                 215                 220

Gly Asp Tyr His Tyr Gly Met Asp Tyr Trp Gly Gln Gly Thr Ser Val
225                 230                 235                 240

Thr Val Ser Ser Glu Leu Lys Thr Pro Leu Gly Asp Thr Thr His Thr
                245                 250                 255

Glu Pro Lys Ser Cys Asp Thr Pro Pro Cys Pro Arg Cys Pro Gly
            260                 265                 270

Gly Gly Ser Ser Gly Gly Gly Ser Gly Gly Gln Pro Arg Glu Pro Gln
            275                 280                 285

Val Tyr Thr Leu Pro Pro Ser Arg Glu Glu Met Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Ser Gly Gln Pro Glu Asn Asn Tyr Asn Thr Thr Pro
                325                 330                 335

Pro Met Leu Asp Ser Asp Gly Ser Phe Phe Leu Tyr Ser Lys Leu Thr
            340                 345                 350

Val Asp Lys Ser Arg Trp Gln Gln Gly Asn Ile Phe Ser Cys Ser Val
            355                 360                 365

Met His Glu Ala Leu His Asn Arg Phe Thr Gln Lys Ser Leu Ser Leu
370                 375                 380

Ser Pro Gly Lys Gly Leu Gly Gly Leu Arg Asp Thr Leu Cys Ile Gly
385                 390                 395                 400

Tyr His Ala Asn Asn Ser Thr Asp Thr Val Asp Thr Val Leu Glu Lys
                405                 410                 415

Asn Val Thr Val Thr His Ser Val Asn Leu Leu Glu Asp Lys His Asn
            420                 425                 430

Gly Lys Leu Cys Lys Leu Arg Gly Val Ala Pro Leu His Leu Gly Lys
            435                 440                 445

Cys Asn Ile Ala Gly Trp Ile Leu Gly Asn Pro Glu Cys Glu Ser Leu
            450                 455                 460

Ser Thr Ala Ser Ser Trp Ser Tyr Ile Val Glu Thr Ser Ser Ser Asp
465                 470                 475                 480

Asn Gly Thr Cys Tyr Pro Gly Asp Phe Ile Asp Tyr Glu Glu Leu Arg
```

```
                485                 490                 495
Glu Gln Leu Ser Ser Val Ser Ser Phe Glu Arg Phe Glu Ile Phe Pro
                500                 505                 510

Lys Thr Ser Ser Trp Pro Asn His Asp Ser Asn Lys Gly Val Thr Ala
                515                 520                 525

Ala Cys Pro His Ala Gly Ala Lys Ser Phe Tyr Lys Asn Leu Ile Trp
    530                 535                 540

Leu Val Lys Lys Gly Asn Ser Tyr Pro Lys Leu Ser Lys Ser Tyr Ile
545                 550                 555                 560

Asn Asp Lys Gly Lys Glu Val Leu Val Leu Trp Gly Ile His His Pro
                565                 570                 575

Ser Thr Ser Ala Asp Gln Gln Ser Leu Tyr Gln Asn Ala Asp Ala Tyr
                580                 585                 590

Val Phe Val Gly Ser Ser Arg Tyr Ser Lys Lys Phe Lys Pro Glu Ile
                595                 600                 605

Ala Ile Arg Pro Lys Val Arg Asp Gln Glu Gly Arg Met Asn Tyr Tyr
                610                 615                 620

Trp Thr Leu Val Glu Pro Gly Asp Lys Ile Thr Phe Glu Ala Thr Gly
625                 630                 635                 640

Asn Leu Val Val Pro Arg Tyr Ala Phe Ala Met Glu Arg Asn Ala Gly
                    645                 650                 655

Ser Gly Ile Ile Ile Ser Asp Thr Pro Val His Asp Cys Asn Thr Thr
                660                 665                 670

Cys Gln Thr Pro Lys Gly Ala Ile Asn Thr Ser Leu Pro Phe Gln Asn
                675                 680                 685

Ile His Pro Ile Thr Ile Gly Lys Cys Pro Lys Tyr Val Lys Ser Thr
                690                 695                 700

Lys Leu Arg Leu Ala Thr Gly Leu Arg Asn Val Pro Ser Ile Gln Ser
705                 710                 715                 720

Arg Gly Leu Phe Gly Ala Ile Ala Gly Phe Ile Glu Gly Gly Trp Thr
                    725                 730                 735

Gly Met Val Asp Gly Trp Tyr Gly Tyr His His Gln Asn Glu Gln Gly
                740                 745                 750

Ser Gly Tyr Ala Ala Asp Leu Lys Ser Thr Gln Asn Ala Ile Asp Glu
                755                 760                 765

Ile Thr Asn Lys Val Asn Ser Val Ile Glu Lys Met Asn Thr Gln Phe
                770                 775                 780

Thr Ala Val Gly Lys Glu Phe Asn His Leu Glu Lys Arg Ile Glu Asn
785                 790                 795                 800

Leu Asn Lys Lys Val Asp Asp Gly Phe Leu Asp Ile Trp Thr Tyr Asn
                    805                 810                 815

Ala Glu Leu Leu Val Leu Leu Glu Asn Glu Arg Thr Leu Asp Tyr His
                820                 825                 830

Asp Ser Asn Val Lys Asn Leu Tyr Glu Lys Val Arg Ser Gln Leu Lys
                835                 840                 845

Asn Asn Ala Lys Glu Ile Gly Asn Gly Cys Phe Glu Phe Tyr His Lys
                850                 855                 860

Cys Asp Asn Thr Cys Met Glu Ser Val Lys Asn Gly Thr Tyr Asp Tyr
865                 870                 875                 880

Pro Lys Tyr Ser Glu Glu Ala Lys Leu Asn Arg Glu Glu Ile Asp Gly
                    885                 890                 895

Val Lys Leu Glu Ser Thr Arg Ile Tyr Gln Ile Leu Ala Ile Tyr Ser
                900                 905                 910
```

Thr Val Ala Ser Ser Leu
        915

<210> SEQ ID NO 15
<211> LENGTH: 523
<212> TYPE: PRT
<213> ORGANISM: Artificial sequence
<220> FEATURE:
<223> OTHER INFORMATION: Synthetic

<400> SEQUENCE: 15

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Asn Gly Val Thr Ala Ala Cys Ser His Glu Gly Lys Ser Ser Phe Tyr
    130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Lys Gly Lys Glu Val Leu Val Leu Trp
                165                 170                 175

Gly Ile His His Pro Pro Asn Ser Lys Glu Gln Gln Asn Leu Tyr Gln
            180                 185                 190

Asn Glu Asn Ala Tyr Val Ser Val Val Thr Ser Asn Tyr Asn Arg Arg
        195                 200                 205

Phe Thr Pro Glu Ile Ala Glu Arg Pro Lys Val Arg Asp Gln Ala Gly
    210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                245                 250                 255

Ser Arg Gly Phe Gly Ser Gly Ile Ile Thr Ser Asn Ala Ser Met His
            260                 265                 270

Glu Cys Asn Thr Lys Cys Gln Thr Pro Leu Gly Ala Ile Asn Ser Ser
        275                 280                 285

Leu Pro Tyr Gln Asn Ile His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Ile Asp Gly Trp Tyr Gly Tyr His His
            340                 345                 350

```
Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Thr Val Ile Glu Lys
    370                 375                 380

Met Asn Ile Gln Phe Thr Ala Val Gly Lys Glu Phe Asn Lys Leu Glu
385                 390                 395                 400

Lys Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Lys Tyr Ser Glu Glu Ser Lys Leu Asn Arg
                485                 490                 495

Glu Lys Val Asp Gly Val Lys Leu Glu Ser Met Gly Ile Tyr Gln Ile
            500                 505                 510

Leu Ala Ile Tyr Ser Thr Val Ala Ser Ser Leu
        515                 520

<210> SEQ ID NO 16
<211> LENGTH: 524
<212> TYPE: PRT
<213> ORGANISM: Artificial sequence
<220> FEATURE:
<223> OTHER INFORMATION: Synthetic

<400> SEQUENCE: 16

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190
```

```
Gln Asn Ala Asp Ala Tyr Val Phe Val Gly Ser Ser Arg Tyr Ser Lys
            195                 200                 205
Lys Phe Lys Pro Glu Ile Ala Ile Arg Pro Lys Val Arg Asp Gln Glu
    210                 215                 220
Gly Arg Met Asn Tyr Tyr Trp Thr Leu Val Glu Pro Gly Asp Lys Ile
225                 230                 235                 240
Thr Phe Glu Ala Thr Gly Asn Leu Val Val Pro Arg Tyr Ala Phe Ala
                245                 250                 255
Met Glu Arg Asn Ala Gly Ser Gly Ile Ile Ile Ser Asp Thr Pro Val
            260                 265                 270
His Asp Cys Asn Thr Thr Cys Gln Thr Pro Lys Gly Ala Ile Asn Thr
        275                 280                 285
Ser Leu Pro Phe Gln Asn Ile His Pro Ile Thr Ile Gly Lys Cys Pro
    290                 295                 300
Lys Tyr Val Lys Ser Thr Lys Leu Arg Leu Ala Thr Gly Leu Arg Asn
305                 310                 315                 320
Ile Pro Ser Ile Gln Ser Arg Gly Leu Phe Gly Ala Ile Ala Gly Phe
                325                 330                 335
Ile Glu Gly Gly Trp Thr Gly Met Val Asp Gly Trp Tyr Gly Tyr His
            340                 345                 350
His Gln Asn Glu Gln Gly Ser Gly Tyr Ala Ala Asp Leu Lys Ser Thr
        355                 360                 365
Gln Asn Ala Ile Asp Glu Ile Thr Asn Lys Val Asn Ser Val Ile Glu
    370                 375                 380
Lys Met Asn Thr Gln Phe Thr Ala Val Gly Lys Glu Phe Asn His Leu
385                 390                 395                 400
Glu Lys Arg Ile Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
            420                 425                 430
Arg Thr Leu Asp Tyr His Asp Ser Asn Val Lys Asn Leu Tyr Glu Lys
        435                 440                 445
Val Arg Ser Gln Leu Lys Asn Asn Ala Lys Glu Ile Gly Asn Gly Cys
    450                 455                 460
Phe Glu Phe Tyr His Lys Cys Asp Asn Thr Cys Met Glu Ser Val Lys
465                 470                 475                 480
Asn Gly Thr Tyr Asp Tyr Pro Lys Tyr Ser Glu Glu Ala Lys Leu Asn
                485                 490                 495
Arg Glu Glu Ile Asp Gly Val Lys Leu Glu Ser Thr Arg Ile Tyr Gln
            500                 505                 510
Ile Leu Ala Ile Tyr Ser Thr Val Ala Ser Ser Leu
        515                 520

<210> SEQ ID NO 17
<211> LENGTH: 511
<212> TYPE: PRT
<213> ORGANISM: Artificial sequence
<220> FEATURE:
<223> OTHER INFORMATION: Synthetic

<400> SEQUENCE: 17

Asp Gln Ile Cys Ile Gly Tyr His Ala Asn Asn Ser Thr Glu Gln Val
1               5                   10                  15
Asp Thr Ile Met Glu Lys Asn Val Thr Val Thr His Ala Gln Asp Ile
            20                  25                  30
```

-continued

```
Leu Glu Arg Thr His Asn Gly Lys Leu Cys Asp Leu Asn Gly Val Lys
         35                  40                  45
Pro Leu Ile Leu Arg Asp Cys Ser Val Ala Gly Trp Leu Leu Gly Asn
 50                  55                  60
Pro Met Cys Asp Glu Phe Ile Asn Val Pro Glu Trp Ser Tyr Ile Val
 65                  70                  75                  80
Glu Lys Ala Ser Pro Ala Asn Asp Leu Cys Tyr Pro Gly Asn Phe Asn
                 85                  90                  95
Asp Tyr Glu Glu Leu Lys His Leu Leu Ser Arg Ile Ser His Phe Glu
                100                 105                 110
Lys Ile Gln Ile Ile Pro Lys Ser Ser Trp Ser Asn His Asp Ala Ser
            115                 120                 125
Ser Gly Val Ser Ser Ala Cys Pro Tyr Leu Gly Lys Ser Ser Phe Phe
        130                 135                 140
Arg Asn Val Val Trp Leu Ile Lys Lys Asn Ser Thr Tyr Pro Thr Ile
145                 150                 155                 160
Lys Arg Ser Tyr Asn Asn Thr Asn Gln Glu Asp Leu Leu Val Leu Trp
                165                 170                 175
Gly Ile His His Pro Asn Asp Ala Ala Glu Gln Thr Lys Leu Tyr Gln
            180                 185                 190
Asn Pro Thr Thr Tyr Ile Ser Val Gly Thr Ser Thr Leu Asn Gln Arg
        195                 200                 205
Leu Val Pro Glu Ile Ala Thr Arg Pro Lys Val Asn Gly Gln Ser Gly
    210                 215                 220
Arg Ile Glu Phe Phe Trp Thr Ile Leu Lys Pro Asn Asp Ala Ile Asn
225                 230                 235                 240
Phe Glu Ser Asn Gly Asn Phe Ile Ala Pro Glu Tyr Ala Tyr Lys Ile
                245                 250                 255
Val Lys Lys Gly Asp Ser Thr Ile Met Lys Ser Glu Leu Glu Tyr Gly
            260                 265                 270
Asn Cys Asn Thr Lys Cys Gln Thr Pro Met Gly Ala Ile Asn Ser Ser
        275                 280                 285
Met Pro Phe His Asn Ile His Pro Leu Thr Ile Gly Glu Cys Pro Lys
    290                 295                 300
Tyr Val Lys Ser Asn Arg Leu Val Leu Ala Thr Gly Leu Arg Asn Ala
305                 310                 315                 320
Pro Gln Arg Glu Lys Arg Gly Leu Phe Gly Ala Ile Ala Gly Phe Ile
                325                 330                 335
Glu Gly Gly Trp Gln Gly Met Val Asp Gly Trp Tyr Gly Tyr His His
            340                 345                 350
Ser Asn Glu Gln Gly Ser Gly Tyr Ala Ala Asp Gln Glu Ser Thr Gln
        355                 360                 365
Lys Ala Ile Asp Gly Val Thr Asn Lys Val Asn Ser Ile Ile Asn Lys
    370                 375                 380
Met Asn Thr Gln Phe Glu Ala Val Gly Lys Glu Phe Asn Asn Leu Glu
385                 390                 395                 400
Arg Arg Ile Glu Asn Leu Asn Lys Lys Met Glu Asp Gly Phe Leu Asp
                405                 410                 415
Val Trp Thr Tyr Asn Ala Glu Leu Leu Val Leu Met Glu Asn Glu Arg
            420                 425                 430
Thr Leu Asp Phe His Asp Ser Asn Val Lys Asn Leu Tyr Asp Lys Val
        435                 440                 445
```

```
Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Lys Asn
465                 470                 475                 480

Gly Thr Tyr Asp Tyr Pro Gln Tyr Ser Glu Glu Ala Arg Leu Asn Arg
                485                 490                 495

Glu Glu Ile Ser Gly Val Lys Leu Glu Ser Met Gly Thr Tyr Gln
                500                 505                 510
```

<210> SEQ ID NO 18
<211> LENGTH: 525
<212> TYPE: PRT
<213> ORGANISM: Artificial sequence
<220> FEATURE:
<223> OTHER INFORMATION: Synthetic

<400> SEQUENCE: 18

```
Asp Lys Ile Cys Ile Gly Tyr His Ala Asn Asn Ser Thr Thr Gln Val
1               5                   10                  15

Asp Thr Ile Leu Glu Lys Asn Val Thr Val Thr His Ser Val Glu Leu
                20                  25                  30

Leu Glu Asn Gln Lys Glu Glu Arg Phe Cys Lys Ile Leu Asn Lys Ala
            35                  40                  45

Pro Leu Asp Leu Arg Gly Cys Thr Ile Glu Gly Trp Ile Leu Gly Asn
50                  55                  60

Pro Gln Cys Asp Leu Leu Leu Gly Asp Gln Ser Trp Ser Tyr Ile Val
65                  70                  75                  80

Glu Arg Pro Thr Ala Gln Asn Gly Ile Cys Tyr Pro Gly Ala Leu Asn
                85                  90                  95

Glu Val Glu Glu Leu Lys Ala Leu Ile Gly Ser Gly Glu Arg Val Glu
            100                 105                 110

Arg Phe Glu Met Phe Pro Lys Ser Thr Trp Thr Gly Val Asp Thr Ser
            115                 120                 125

Ser Gly Val Thr Lys Ala Cys Pro Tyr Asn Ser Gly Ser Ser Phe Tyr
130                 135                 140

Arg Asn Leu Leu Trp Ile Ile Lys Thr Lys Ser Ala Ala Tyr Pro Val
145                 150                 155                 160

Ile Lys Gly Thr Tyr Asn Asn Thr Gly Ser Gln Pro Ile Leu Tyr Phe
                165                 170                 175

Trp Gly Val His His Pro Pro Asp Thr Asn Glu Gln Asn Thr Leu Tyr
            180                 185                 190

Gly Ser Gly Asp Arg Tyr Val Arg Met Gly Thr Glu Ser Met Asn Phe
            195                 200                 205

Ala Lys Ser Pro Glu Ile Ala Ala Arg Pro Ala Val Asn Gly Gln Arg
210                 215                 220

Gly Arg Ile Asp Tyr Tyr Trp Ser Val Leu Lys Pro Gly Glu Thr Leu
225                 230                 235                 240

Asn Val Glu Ser Asn Gly Asn Leu Ile Ala Pro Trp Tyr Ala Tyr Lys
                245                 250                 255

Phe Val Ser Thr Asn Asn Lys Gly Ala Ile Phe Lys Ser Asn Leu Pro
            260                 265                 270

Ile Glu Asn Cys Asp Ala Thr Cys Gln Thr Ile Ala Gly Val Leu Arg
            275                 280                 285

Thr Asn Lys Thr Phe Gln Asn Val Ser Pro Leu Trp Ile Gly Glu Cys
290                 295                 300
```

```
Pro Lys Tyr Val Lys Ser Glu Ser Leu Arg Leu Ala Thr Gly Leu Arg
305                 310                 315                 320

Asn Val Pro Gln Ile Glu Thr Arg Gly Leu Phe Gly Ala Ile Ala Gly
            325                 330                 335

Phe Ile Glu Gly Gly Trp Thr Gly Met Ile Asp Gly Trp Tyr Gly Tyr
        340                 345                 350

His His Glu Asn Ser Gln Gly Ser Gly Tyr Ala Ala Asp Lys Glu Ser
    355                 360                 365

Thr Gln Lys Ala Ile Asp Gly Ile Thr Asn Lys Val Asn Ser Ile Ile
370                 375                 380

Asp Lys Met Asn Thr Gln Phe Glu Ala Val Asp His Glu Phe Ser Asn
385                 390                 395                 400

Leu Glu Arg Arg Ile Asp Asn Leu Asn Lys Arg Met Glu Asp Gly Phe
                405                 410                 415

Leu Asp Val Trp Thr Tyr Asn Ala Glu Leu Leu Val Leu Leu Glu Asn
            420                 425                 430

Glu Arg Thr Leu Asp Leu His Asp Ala Asn Val Lys Asn Leu Tyr Glu
        435                 440                 445

Lys Val Lys Ser Gln Leu Arg Asp Asn Ala Asn Asp Leu Gly Asn Gly
450                 455                 460

Cys Phe Glu Phe Trp His Lys Cys Asp Asn Glu Cys Ile Glu Ser Val
465                 470                 475                 480

Lys Asn Gly Thr Tyr Asp Tyr Pro Lys Tyr Gln Asp Glu Ser Lys Leu
                485                 490                 495

Asn Arg Gln Glu Ile Glu Ser Val Lys Leu Asp Asn Leu Gly Val Tyr
            500                 505                 510

Gln Ile Leu Ala Ile Tyr Ser Thr Val Ser Ser Ser Leu
        515                 520                 525

<210> SEQ ID NO 19
<211> LENGTH: 524
<212> TYPE: PRT
<213> ORGANISM: Artificial sequence
<220> FEATURE:
<223> OTHER INFORMATION: Synthetic

<400> SEQUENCE: 19

Asp Arg Ile Cys Ile Gly Tyr Gln Ser Asn Asn Ser Thr Asp Thr Val
1               5                   10                  15

Asn Thr Leu Ile Glu Gln Asn Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met Cys Tyr Pro Gly Ser Ile Glu
                85                  90                  95

Asn Leu Glu Glu Leu Arg Phe Val Phe Ser Ser Ala Ala Ser Tyr Lys
            100                 105                 110

Arg Ile Arg Leu Phe Asp Tyr Ser Arg Trp Asn Val Thr Arg Ser Gly
        115                 120                 125

Thr Ser Lys Ala Cys Asn Ala Ser Thr Gly Gly Gln Ser Phe Tyr Arg
    130                 135                 140
```

```
Ser Ile Asn Trp Leu Thr Lys Lys Pro Asp Thr Tyr Asp Phe Asn
145                 150                 155                 160

Glu Gly Thr Tyr Val Asn Asn Glu Asp Gly Asp Ile Ile Phe Leu Trp
                165                 170                 175

Gly Ile His His Pro Asp Thr Lys Glu Gln Thr Thr Leu Tyr Lys
            180                 185                 190

Asn Ala Asn Thr Leu Thr Ser Val Thr Thr Asn Thr Ile Asn Arg Asn
        195                 200                 205

Phe Gln Pro Asn Ile Gly Pro Arg Pro Leu Val Arg Gly Gln Gln Gly
    210                 215                 220

Arg Met Asp Tyr Tyr Trp Gly Ile Leu Lys Arg Gly Glu Thr Leu Lys
225                 230                 235                 240

Ile Arg Thr Asn Gly Asn Leu Ile Ala Pro Glu Phe Gly Tyr Leu Leu
                245                 250                 255

Lys Gly Glu Ser His Gly Arg Ile Ile Gln Asn Glu Asp Ile Pro Ile
            260                 265                 270

Gly Asn Cys Asn Thr Lys Cys Gln Thr Tyr Ala Gly Ala Ile Asn Ser
        275                 280                 285

Ser Lys Pro Phe Gln Asn Ala Ser Arg His Tyr Met Gly Glu Cys Pro
    290                 295                 300

Lys Tyr Val Lys Lys Ala Ser Leu Arg Leu Ala Val Gly Leu Arg Asn
305                 310                 315                 320

Thr Pro Ser Val Glu Pro Arg Gly Leu Phe Gly Ala Ile Ala Gly Phe
                325                 330                 335

Ile Glu Gly Gly Trp Ser Gly Met Ile Asp Gly Trp Tyr Gly Phe His
            340                 345                 350

His Ser Asn Ser Glu Gly Thr Gly Met Ala Ala Asp Gln Lys Ser Thr
        355                 360                 365

Gln Glu Ala Ile Asp Lys Ile Thr Asn Lys Val Asn Asn Ile Val Asp
    370                 375                 380

Lys Met Asn Arg Glu Phe Glu Val Val Asn His Glu Phe Ser Glu Val
385                 390                 395                 400

Glu Lys Arg Ile Asn Met Ile Asn Asp Lys Ile Asp Asp Gln Ile Glu
                405                 410                 415

Asp Leu Trp Ala Tyr Asn Ala Glu Leu Leu Val Leu Leu Glu Asn Gln
            420                 425                 430

Lys Thr Leu Asp Glu His Asp Ser Asn Val Lys Asn Leu Phe Asp Glu
        435                 440                 445

Val Lys Arg Arg Leu Ser Ala Asn Ala Ile Asp Ala Gly Asn Gly Cys
    450                 455                 460

Phe Asp Ile Leu His Lys Cys Asp Asn Glu Cys Met Glu Thr Ile Lys
465                 470                 475                 480

Asn Gly Thr Tyr Asn His Lys Glu Tyr Glu Glu Ala Lys Leu Glu
                485                 490                 495

Arg Ser Lys Ile Asn Gly Val Lys Leu Glu Glu Asn Thr Thr Tyr Lys
            500                 505                 510

Ile Leu Ser Ile Tyr Ser Thr Val Ala Ala Ser Leu
        515                 520

<210> SEQ ID NO 20
<211> LENGTH: 517
<212> TYPE: PRT
<213> ORGANISM: Artificial sequence
<220> FEATURE:
<223> OTHER INFORMATION: Synthetic
```

<400> SEQUENCE: 20

Asp Lys Ile Cys Ile Gly His Gln Ser Thr Asn Ser Thr Glu Thr Val
1               5                   10                  15

Asp Thr Leu Thr Glu Thr Asn Val Pro Val Thr His Ala Lys Glu Leu
            20                  25                  30

Leu His Thr Glu His Asn Gly Met Leu Cys Ala Thr Ser Leu Gly His
        35                  40                  45

Pro Leu Ile Leu Asp Thr Cys Thr Ile Glu Gly Leu Val Tyr Gly Asn
    50                  55                  60

Pro Ser Cys Asp Leu Leu Leu Gly Gly Arg Glu Trp Ser Tyr Ile Val
65                  70                  75                  80

Glu Arg Ser Ser Ala Val Asn Gly Thr Cys Tyr Pro Gly Asn Val Glu
                85                  90                  95

Asn Leu Glu Glu Leu Arg Thr Leu Phe Ser Ser Ala Ser Ser Tyr Gln
            100                 105                 110

Arg Ile Gln Ile Phe Pro Asp Thr Thr Trp Asn Val Thr Tyr Thr Gly
        115                 120                 125

Thr Ser Arg Ala Cys Ser Gly Ser Phe Tyr Arg Ser Met Arg Trp Leu
    130                 135                 140

Thr Gln Lys Ser Gly Phe Tyr Pro Val Gln Asp Ala Gln Tyr Thr Asn
145                 150                 155                 160

Asn Arg Gly Lys Ser Ile Leu Phe Val Trp Gly Ile His His Pro Pro
                165                 170                 175

Thr Tyr Thr Glu Gln Thr Asn Leu Tyr Ile Arg Asn Asp Thr Thr Thr
            180                 185                 190

Ser Val Thr Thr Glu Asp Leu Asn Arg Thr Phe Lys Pro Val Ile Gly
        195                 200                 205

Pro Arg Pro Leu Val Asn Gly Leu Gln Gly Arg Ile Asp Tyr Tyr Trp
    210                 215                 220

Ser Val Leu Lys Pro Gly Gln Thr Leu Arg Val Arg Ser Asn Gly Asn
225                 230                 235                 240

Leu Ile Ala Pro Trp Tyr Gly His Val Leu Ser Gly Gly Ser His Gly
                245                 250                 255

Arg Ile Leu Lys Thr Asp Leu Lys Gly Gly Asn Cys Val Val Gln Cys
            260                 265                 270

Gln Thr Glu Lys Gly Gly Leu Asn Ser Thr Leu Pro Phe His Asn Ile
        275                 280                 285

Ser Lys Tyr Ala Phe Gly Thr Cys Pro Lys Tyr Val Arg Val Asn Ser
    290                 295                 300

Leu Lys Leu Ala Val Gly Leu Arg Asn Val Pro Ala Arg Ser Ser Arg
305                 310                 315                 320

Gly Leu Phe Gly Ala Ile Ala Gly Phe Ile Glu Gly Gly Trp Pro Gly
                325                 330                 335

Leu Val Ala Gly Trp Tyr Gly Phe Gln His Ser Asn Asp Gln Gly Val
            340                 345                 350

Gly Met Ala Ala Asp Arg Asp Ser Thr Gln Lys Ala Ile Asp Lys Ile
        355                 360                 365

Thr Ser Lys Val Asn Asn Ile Val Asp Lys Met Asn Lys Gln Tyr Glu
    370                 375                 380

Ile Ile Asp His Glu Phe Ser Glu Val Glu Thr Arg Leu Asn Met Ile
385                 390                 395                 400

Asn Asn Lys Ile Asp Asp Gln Ile Gln Asp Val Trp Ala Tyr Asn Ala

```
                    405                 410                 415
Glu Leu Val Leu Glu Asn Gln Lys Thr Leu Asp Glu His Asp
            420                 425                 430

Ala Asn Val Asn Leu Tyr Asn Lys Val Lys Arg Ala Leu Gly Ser
        435                 440                 445

Asn Ala Met Glu Asp Gly Lys Gly Cys Phe Glu Leu Tyr His Lys Cys
    450                 455                 460

Asp Asp Gln Cys Met Glu Thr Ile Arg Asn Gly Thr Tyr Asn Arg Arg
465                 470                 475                 480

Lys Tyr Arg Glu Glu Ser Arg Leu Glu Arg Gln Lys Ile Glu Gly Val
                485                 490                 495

Lys Leu Glu Ser Glu Gly Thr Tyr Lys Ile Leu Thr Ile Tyr Ser Thr
            500                 505                 510

Val Ala Ser Ser Leu
            515

<210> SEQ ID NO 21
<211> LENGTH: 524
<212> TYPE: PRT
<213> ORGANISM: Artificial sequence
<220> FEATURE:
<223> OTHER INFORMATION: Synthetic

<400> SEQUENCE: 21

Asp Glu Ile Cys Ile Gly Tyr Leu Ser Asn Asn Ser Thr Asp Lys Val
1               5                   10                  15

Asp Thr Ile Ile Glu Asn Asn Val Thr Val Thr Ser Ser Val Glu Leu
            20                  25                  30

Val Glu Thr Glu His Thr Gly Ser Phe Cys Ser Ile Asn Gly Lys Gln
        35                  40                  45

Pro Ile Ser Leu Gly Asp Cys Ser Phe Ala Gly Trp Ile Leu Gly Asn
    50                  55                  60

Pro Met Cys Asp Asp Leu Ile Gly Lys Thr Ser Trp Ser Tyr Ile Val
65                  70                  75                  80

Glu Lys Pro Asn Pro Thr Asn Gly Ile Cys Tyr Pro Gly Ile Leu Glu
                85                  90                  95

Asn Glu Glu Glu Leu Arg Leu Lys Phe Ser Gly Val Leu Glu Phe Asn
            100                 105                 110

Lys Phe Glu Ala Phe Thr Ser Asn Gly Trp Gly Ala Val Asn Ser Gly
        115                 120                 125

Ala Gly Val Thr Ala Ala Cys Lys Phe Gly Ser Ser Asn Ser Phe Phe
    130                 135                 140

Arg Asn Met Ile Trp Leu Ile His Gln Ser Gly Thr Tyr Pro Val Ile
145                 150                 155                 160

Lys Arg Thr Phe Asn Asn Thr Lys Gly Arg Asp Val Leu Val Val Trp
                165                 170                 175

Gly Ile His His Pro Ala Thr Leu Lys Glu His Gln Asp Leu Tyr Lys
            180                 185                 190

Lys Asp Ser Ser Tyr Val Ala Val Gly Ser Glu Thr Tyr Asn Arg Arg
        195                 200                 205

Phe Thr Pro Glu Ile Ser Thr Arg Pro Lys Val Asn Gly Gln Ala Gly
    210                 215                 220

Arg Met Thr Phe Tyr Trp Thr Ile Val Lys Pro Gly Glu Ser Ile Thr
225                 230                 235                 240

Phe Glu Ser Asn Gly Ala Phe Leu Ala Pro Arg Tyr Ala Phe Glu Ile
```

```
                        245                 250                 255
Val Ser Val Gly Asn Gly Lys Leu Phe Arg Ser Glu Leu Asn Ile Glu
            260                 265                 270

Ser Cys Ser Thr Lys Cys Gln Thr Glu Val Gly Gly Ile Asn Thr Asn
            275                 280                 285

Lys Ser Phe His Ser Val His Arg Asn Thr Ile Gly Asp Cys Pro Lys
            290                 295                 300

Tyr Val Asn Val Lys Ser Leu Lys Leu Ala Thr Gly Leu Arg Asn Val
305                 310                 315                 320

Pro Ala Ile Ala Ser Arg Gly Leu Phe Gly Ala Ile Ala Gly Phe Ile
                325                 330                 335

Glu Gly Gly Trp Pro Gly Leu Ile Asn Gly Trp Tyr Gly Phe Gln His
                340                 345                 350

Arg Asn Glu Glu Gly Thr Gly Ile Ala Ala Asp Lys Glu Ser Thr Gln
                355                 360                 365

Lys Ala Ile Asp Gln Ile Thr Ser Lys Val Asn Asn Ile Val Asp Arg
                370                 375                 380

Met Asn Thr Asn Phe Glu Ser Val Gln His Glu Phe Ser Glu Ile Glu
385                 390                 395                 400

Glu Arg Ile Asn Arg Leu Ser Lys His Val Asp Asp Ser Val Val Asp
                        405                 410                 415

Ile Trp Ser Tyr Asn Ala Gln Leu Leu Val Leu Leu Glu Asn Glu Lys
                420                 425                 430

Thr Leu Asp Leu His Asp Ser Asn Val Arg Asn Leu His Glu Arg Val
                435                 440                 445

Arg Arg Met Leu Lys Asp Asn Ala Lys Asp Glu Gly Asn Gly Cys Phe
            450                 455                 460

Thr Phe Tyr His Lys Cys Asp Asn Glu Cys Ile Glu Lys Val Arg Asn
465                 470                 475                 480

Gly Thr Tyr Asp His Lys Glu Phe Glu Lys Glu Ser Lys Ile Asn Arg
                        485                 490                 495

Gln Glu Ile Glu Gly Val Lys Leu Asp Ser Ser Gly Asn Val Tyr Lys
                500                 505                 510

Ile Leu Ser Ile Tyr Ser Cys Ile Ala Ser Ser Leu
                515                 520

<210> SEQ ID NO 22
<211> LENGTH: 522
<212> TYPE: PRT
<213> ORGANISM: Artificial sequence
<220> FEATURE:
<223> OTHER INFORMATION: Synthetic

<400> SEQUENCE: 22

Asp Arg Ile Cys Val Gly Tyr Leu Ser Thr Asn Ser Ser Glu Arg Val
1               5                   10                  15

Asp Thr Leu Leu Glu Asn Asn Val Pro Val Thr Ser Ser Val Asp Leu
                20                  25                  30

Val Glu Thr Asn His Thr Gly Thr Tyr Cys Ser Leu Gly Gly Ile Ser
            35                  40                  45

Pro Val His Leu Gly Asp Cys Ser Phe Glu Gly Trp Ile Val Gly Asn
            50                  55                  60

Pro Ala Cys Ala Ser Asn Leu Gly Ile Arg Glu Trp Ser Tyr Leu Ile
65                  70                  75                  80

Glu Asp Pro Ser Ala Pro His Gly Leu Cys Tyr Pro Gly Glu Leu Asp
```

```
            85                  90                  95
Asn Asn Gly Glu Leu Arg His Leu Phe Ser Gly Ile Arg Ser Phe Ser
            100                 105                 110

Arg Thr Glu Leu Ile Ala Pro Thr Ser Trp Gly Ala Val Asn Asp Gly
            115                 120                 125

Val Ser Ser Ala Cys Gln Asp Lys Gly Ala Ser Ser Phe Tyr Arg Asn
            130                 135                 140

Leu Val Trp Phe Val Glu Arg Gly Asn Lys Tyr Pro Val Ile Arg Gly
145                 150                 155                 160

Thr Tyr Asn Asn Thr Thr Gly Arg Asp Val Leu Val Ile Trp Gly Ile
                165                 170                 175

His His Pro Val Ser Thr Asp Glu Ala Arg Lys Leu Tyr Val Asn Asp
            180                 185                 190

Asn Pro Tyr Thr Leu Val Ser Thr Ser Ser Trp Ser Arg Lys Tyr Asn
            195                 200                 205

Leu Glu Ile Gly Ile Arg Pro Gly Tyr Asn Gly Gln Lys Ser Trp Met
            210                 215                 220

Lys Ile Tyr Trp Tyr Leu Met His Pro Gly Glu Ser Ile Ser Phe Glu
225                 230                 235                 240

Ser Asn Gly Gly Leu Leu Ala Pro Lys Tyr Gly Tyr Ile Ile Glu Glu
                245                 250                 255

Tyr Gly Lys Gly Arg Ile Phe Gln Ser Arg Ile Arg Ile Ala Lys Cys
                260                 265                 270

Asn Thr Lys Cys Gln Thr Ser Val Gly Gly Ile Asn Thr Asn Lys Thr
            275                 280                 285

Phe Gln Asn Ile Glu Arg Asn Ala Leu Gly Asp Cys Pro Lys Tyr Ile
            290                 295                 300

Lys Ser Gly Gln Leu Lys Leu Ala Thr Gly Leu Arg Asn Val Pro Ala
305                 310                 315                 320

Ile Ser Lys Arg Gly Leu Phe Gly Ala Ile Ala Gly Phe Ile Glu Gly
                325                 330                 335

Gly Trp Pro Gly Leu Ile Asn Gly Trp Tyr Gly Phe Gln His Gln Asn
                340                 345                 350

Glu Gln Gly Val Gly Met Ala Ala Asp Lys Glu Ser Thr Gln Lys Ala
            355                 360                 365

Ile Asp Gln Ile Thr Thr Lys Ile Asn Asn Ile Ile Glu Lys Met Asn
370                 375                 380

Gly Asn Tyr Asp Ser Ile Arg Gly Glu Phe Ser Gln Val Glu Gln Arg
385                 390                 395                 400

Ile Asn Met Leu Ala Asp Arg Ile Asp Asp Ala Val Thr Asp Val Trp
                405                 410                 415

Ser Tyr Asn Ala Lys Leu Leu Val Leu Leu Glu Asn Asp Lys Thr Leu
                420                 425                 430

Asp Met His Asp Ala Asn Val Arg Asn Leu His Asp Gln Val Arg Arg
            435                 440                 445

Val Leu Lys Thr Asn Ala Ile Asp Glu Gly Asn Gly Cys Phe Glu Leu
            450                 455                 460

Leu His Lys Cys Asn Asp Ser Cys Met Glu Thr Ile Arg Asn Gly Thr
465                 470                 475                 480
```

-continued

```
Tyr Asn His Thr Glu Tyr Glu Glu Glu Ser Lys Leu Lys Arg Gln Glu
                485                 490                 495

Ile Glu Gly Ile Lys Leu Lys Ser Asp Asp Ser Val Tyr Lys Ala Leu
            500                 505                 510

Ser Ile Tyr Ser Cys Ile Ala Ser Ser Ile
        515                 520
```